US008222487B2

(12) United States Patent
Lin et al.

(10) Patent No.: US 8,222,487 B2
(45) Date of Patent: Jul. 17, 2012

(54) APPLICATION OF ERF GENES FROM *BUPLEURUM KAOI*

(75) Inventors: Tsai-Yun Lin, Hsinchu (TW); Wen-Yu Liu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 468 days.

(21) Appl. No.: 12/501,146

(22) Filed: Jul. 10, 2009

(65) Prior Publication Data

US 2010/0251422 A1 Sep. 30, 2010

(30) Foreign Application Priority Data

Mar. 26, 2009 (TW) .............................. 98109978 A

(51) Int. Cl.
*A01H 1/00* (2006.01)
*A01H 5/00* (2006.01)
*C12N 15/09* (2006.01)
*C12N 15/29* (2006.01)
*C12N 15/82* (2006.01)

(52) U.S. Cl. ........ 800/279; 800/278; 800/298; 800/306; 800/314; 800/317.1; 800/301; 435/69.1; 435/419; 435/252.1; 435/468; 536/23.6; 536/23.1

(58) Field of Classification Search ........................ None
See application file for complete search history.

(56) References Cited

U.S. PATENT DOCUMENTS

2005/0155117 A1* 7/2005 Century et al. ............... 800/301

FOREIGN PATENT DOCUMENTS

TW 474790 6/1998

OTHER PUBLICATIONS

Chen et al. Plant Sci (2007), vol. 173 (1),pp. 12-24.*
He et al. Mol Plant Microbe Interact (2001), vol. 14(12):1453-1457.*
Bower et al. Nucleic Acids Research (2010) 38 (21): e194.*
Gu et al. The Plant Cell (2002) 14: 817-831.*
Sujon Sarowar et al., Overexpression of lipid transfer protein (LTP) genes enhances resistance to plant pathogens and LTP functions in long-distance systemic signaling in tobacco, Plant Cell Rep, 2009, pp. 419-427, vol. 28.
Pilar Navarro et al., In vivo anti-inflammatory activity of saponins from *Bupleurum rotundifolium*, Life Sciences, 2001, pp. 1199-1206, vol. 68.
Xiu-Qin Li et al., High Performance Liquid Chromatographic Assay of Saikosaponins fromRadix Bupleuri in China, Biol. Pharm. Bull., 2005, pp. 1736-1742, vol. 28, No. 9.
Shujun Chang et al., A Simple and Efficient Method for Isolating RNA from Pine Trees, Plant Molecular Biology Reporter, 1993, pp. 113-116, vol. 11, No. 2.
Yuko Sasaki et al., Monitoring of Methyl Jasmonate-responsive Genes in Arabidopsis by cDNA Macroarray: Self-activation of Jasmonic Acid Biosynthesis and Crosstalk with Other Phytohormone Signaling Pathways, DNA Research, 2001, pp. 153-161, vol. 8.
Melissa A. Melan et al., An *Arabidopsis thaliana* Lipoxygenase Gene Can Be Induced by Pathogens, Abscisic Acid, and Methyl Jasmonate, Plant Physiol., 1993, pp. 441-450, vol. 101.
Steven J. Clough et al., Floral dip: a simplified method for Agrobacterium-mediated transformation of *Arabidopsis thaliana*, The Plant Journal, 1998, pp. 735-743, vol. 16, No. 6.

* cited by examiner

*Primary Examiner* — Medina A Ibrahim
(74) *Attorney, Agent, or Firm* — WPAT, P.C.; Anthony King

(57) ABSTRACT

The use of *Bupleurum kaoi* ERF gene in controlling diseases caused by pathogen is provided. The gene with pathogen-resistance is inserted into an appropriate vector, and transformed into plants to enhance the pathogen-resistance so as to attain the purpose of controlling the related diseases. This invention can be applied to the agricultural industry, the pharmaceutical industry, and the food industry.

9 Claims, 19 Drawing Sheets

5 min, 1, 2, 8, 24 h 2, 4, 6, 8 d 2, 3, 4, 5 wk 5 wk

APPLICATION OF ERF GENES FROM *BUPLEURUM KAOI*

FIELD OF THE INVENTION

The scope of the present invention is plant molecular biology, especially about substances in transcriptional regulation: characterization of regulatory sequences in regulating the plant tissue of downstream genes, which can react against the invasion of pathogens, an inducer and other induced stress of adversity.

BACKGROUND OF THE INVENTION

In nature, plants often grow in two external adverse conditions including biological and abiotic stress, the former one contains the invasion of fungi, bacteria, viruses and other microorganisms or insects, while the latter contains cold damage, salt damage, light damage and other non-biology stress. The special external structures of plants, such as cuticular layer, cork layer, or wax membrane, provide plants an early barrier of physical defense and protect fragile tissue from external environment. Plants can detect the existence of pathogens directly through cell membrane receptors such as receptor-like kinase and histidine kinase, or detect indirectly through some inducers such as oligosaccharide, lipid polysaccharides, glycopeptides and peptides from plants or pathogens, to trigger a cascade of defense mechanisms, including the generation of defense messages, the accumulation of antibiotics or disease-related proteins. At present, these defences deem to have the following physiological functions: 1. repairing the damaged plant tissues, 2. involving in message regulation of defense mechanism, 3. producing substances which can inhibit pathogens, insects, or other potential harmful substance to the plant growth, 4. regulating plant metabolism. Kwon S J et al. also published that GDLS lipase-like 1 regulates systemic resistance which is dependent on ethylene signaling.

With the understanding of the plant pathogens and molecular level of defense mechanism, human can apply the molecular genetics as a tool to breeding in order to achieve effective control of plant pest. The farmers in the United Kingdom use weak tobacco mosaic virus for greenhouse tomato to prevent damage caused by virus for a long time. Brazilian farmers use citrus tristeza virus which do not produce symptoms to protect citrus plants and New Zealand farmers use apple mosaic virus to do similar prevention work to avoid substantial losses caused by virus infection. In the end of the twentieth century, researchers have found that plants which express special virus protein can prevent disease. However, the method cannot defense exclusively and may probably generate new virus. Following researchers try to find the pathogen defense mechanism in plants and improve the strength of reaction to create plants resistant to pests. TW 149283 claims the use of sweet potato sporamic gene inserted in to a vector and transform into *Agrobateria*, then use *Agrobacteria* as a medium to infect plants to enhance the ability of insect-resistance. Sarowar S. et al. published in 2008 pointed out that overexpression of lipid transfer protein (LTP) can elevate plants resistance to pathogens, and the function of LTP is long-distance systemic signaling in plants (Sarowar S. et al., Plant Cell Rep. 28 (2009) pp. 419-427).

*Bupleurum kaoi* Liu, Chao et Chuang is a species endemic to Taiwan that has 12 pairs of chromosomes and a genome size of about $7.3\times10^8$ bp per copy. Bupleurum roots have been reported to possess anti-inflammatory activity (Navarro P. et al., Life Sci. 68 (2001) 1199-1206) and antihepatotoxic effects. Extracting pharmacological agents from roots of intact plants or from tissue-cultured roots is of interest.

Ethylene-responsive element binding factors (ERFs) are a member of downstream ethylene signaling pathway, which can enhance plant resistance against pathogen.

SUMMARY OF THE INVENTION

The present invention provides a polynucleotide having SEQ ID NO: 1, SEQ ID NO: 2 or SEQ ID NO: 3.

The present invention also provides a method of generating a transgenic plant having enhanced pathogen resistance and inhibition, comprising inserting the polynucleotide (SEQ ID NO: 1, SEQ ID NO: 2 or SEQ ID NO: 3) of the present invention into a vector, transforming the vector into a microorganism, which is introduced into the plant using microorganism-mediated transformation.

The present invention further provides a transgenic plant, which is prepared by the method of the present invention.

DETAILED DESCRIPTION OF THE INVENTION

Figure 1A:
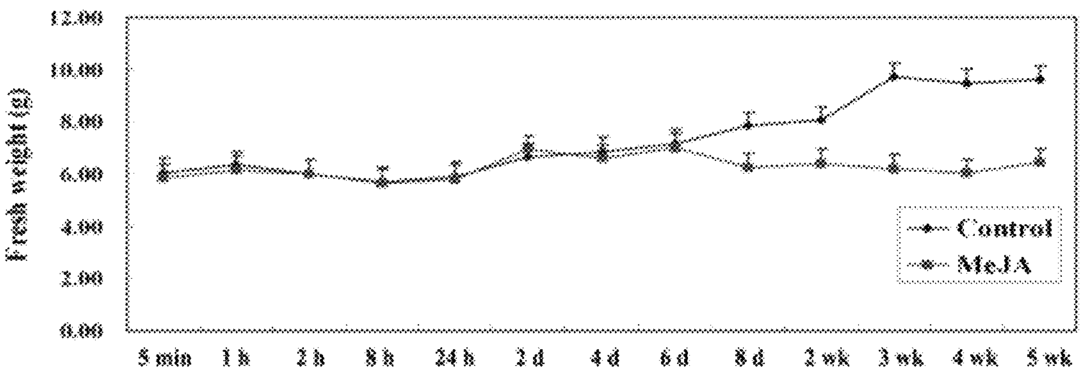
FIG. 1 Effect of MeJA on fresh weight and appearance of *B. kaoi* adventitious roots. (A) Four weeks after subculture, the nutrient medium of *B. kaoi* adventitious roots was refreshed. MeJA (500 μM) was applied 2 weeks after refreshment. The fresh weights of adventitious roots were measured at 13 time points after MeJA treatment as indicated. (B) Adventitious roots treated with MeJA began to show dark brownish pigmentation after 2 weeks. Each panel is a representative of the adventitious roots at the indicated time points. The left and right flasks for each sub-panel indicate the control and MeJA treated adventitious roots, respectively. (C) $H_2O_2$ level and (D) MDA level were measured at the indicated time. Vertical bars indicate S.E. of the mean for n=3.

The main techniques of the present invention are the establishment and screening of the cDNA database, DNA sequencing and analysis, construction of transgenic strains, and pathogen analysis of the *Bupleurum kaoi*. The present invention is mainly about the gene screening and analysis against the *B. kaoi* which is activated, and then isolates the message RNA of BkERFs to get the complementary DNA. After insertion of the cDNA into the binary vector, and then transforms the vector into *Agrobacterium* to infect *Arabidopsis* to obtain transformation plants, which can express BkERFs genes stably and have the elevated ability to resist pathogens.

The present invention uses germ-free seedlings of *B. kaoi* to induce adventitious roots, and treats roots with a plant signal molecule-"Methyl jasmonate" to induce gene expression, enhance saikosaponin production and reduce the growth of adventitious roots. Another goal of the invention is to provide ethylene response factor (BkERFs) gene sequence of *B. kaoi*. The "BkERFs" used herein is any sequence of SEQ ID NO. 1, SEQ ID NO. 2 or SEQ ID NO. 3. The experiments show that overexpression of the BkERFs in cells of *B. kaoi* elevates the expression of pathogen-related genes (PR genes), which are the known PR genes regulated by ethylene response factor of plants. In the present invention, the elevated PR genes of *B. kaoi* cells include but is not limited to BkPDF, BkPR1, BKPR3 and BkPR5 genes.

Another purpose of the present invention is to provide a vector which is used to elevate plant resistance. The vector is prepared by incorporating the BkERFs genes in to it, in another words, is to incorporate the SEQ ID NO. 1, SEQ ID NO. 2 or SEQ ID NO. 3 into the vector. The more preferable vector includes but is not limited to plant transformation binary vector. The present invention also provides a transformation appropriate microorganism as a media to transfect the vector which can elevate plant resistance into plants as a microorganism which can be used to elevate plant resistance. In the present invention, the microorganism includes but is not limited to bacteria, and the preferable microorganism is *Agrobacterium*, the more preferable embodiment is *Agrobacterium tumefaciens.*

The present invention further provides a method of generating a transgenic plant having enhanced pathogen resistance and inhibition, comprising inserting the polynucleotide (SEQ ID NO: 1, SEQ ID NO: 2 or SEQ ID NO: 3) of the present invention into a vector, transforming the vector into a microorganism, which is introduced into the plant using microorganism-mediated transformation. In the present invention, the preferable vector is binary vector, and in a more preferable embodiment, the vector is binary vector pMON530. The microorganism in the present invention includes but is not limited to bacteria, and the preferable microorganism is *Agrobacterium*, the more preferable embodiment is *Agrobacterium tumefaciens.*

The present invention further provides a vector having the effect of bacteria inhibition, wherein the vector is inserted with BkERFs genes, in another words, is to insert SEQ ID NO. 1, SEQ ID NO. 2 or SEQ ID NO. 3 of the present invention into a vector. The preferable vector includes but is not limited to binary vector of plant transformation, and in a more preferable embodiment, the vector is binary vector pMON530. Overexpresssion of the BkERFs after transfection the vector into *B. kaoi* cells, it is found that the *B. kaoi* cells have the effect of bacteria inhibition. In a preferable embodiment, the bacteria inhibition includes but is not limited to *Staphylococcus* and *Pseudomonas*, and the more preferable embodiment, the inhibition is *Staphylococcus aureus* and *Pseudomonas syringae.*

The present invention further provides a method of enhancing bacteria inhibition in a plant, comprising transforming said vector into a microorganism, which is introduced into the plant using microorganism-mediated transformation to enhance bacteria inhibition of the plant. In the present invention, the preferable vector is binary vector, and in a more preferable embodiment, the vector is binary vector pMON530. The microorganism in the present invention includes but is not limited to bacteria, and the preferable microorganism is *Agrobacterium*, the more preferable embodiment is *Agrobacterium tumefaciens.*

Another purpose of the present invention is to provide a transgenic plant, which is prepared by said method of the present invention. The plant can overexpress BkERFs and elevate the translation of pathogen-related genes to have the effect of bacteria inhibition. In the present invention, the preferable plant includes but is not limited to *Bupleurum, Arabidopsis*, cotton, oat, pepper or sugarcane, and in a more preferable embodiment, the plant is *Arabidopsis*. Expression of many pathogen-resistant genes are elevated as the *Arabidopsis* plants express the BkERFs, wherein the elevated pathogen-resistant genes include but is not limited to defensin, AtPR1, AtPR2, AtPR4 and AtPR5.

EXAMPLE

The examples below are non-limiting and are merely representative of various aspects and features of the present invention.

Example 1

Materials and Methods

Plant Growth and Treatment

Adventitious root cultures were induced from the roots of germ-free seedlings of *B. kaoi* and were subcultured every 6 weeks by adding 0.2 g roots to a 125 ml flask containing 50 ml of B5 liquid medium supplemented with 2 mg $l^{-1}$ NAA. Cultures were shaken using a rotary shaker at 100 rpm at 25° C. in the dark. To quantify the effect of MeJA on saikosaponin level, adventitious roots were treated with 500 and 1000 μM MeJA 2 weeks after subculture. Total saikosaponin was measured 2 weeks after MeJA treatment. To monitor expression of MeJA-responsive genes, the nutrient medium was refreshed 4 weeks after subculture and MeJA (500 μM) was applied 2 weeks after refreshment. Roots were harvested at 13 time points (5 min; 1, 2, 8, 24 hours; 2, 4, 6, 8 days; 2, 3, 4, 5 weeks) after the addition of the MeJA.

Measurement of $H_2O_2$ and Malondialdehyde (MDA)

To test whether MeJA caused oxidative stress, the $H_2O_2$ level was measured as described below. $H_2O_2$ was extracted by homogenizing 0.3 to 0.5 g of adventitious roots with 3 ml phosphate buffer (50 mM, pH6.8) and centrifuged at 6000×g for 25 min. A 2 ml extract was mixed with 1 ml 0.1% titanium sulfate in 20% $H_2SO_4$ (v/v), and centrifuged at 6000×g for 15 min. The optical density of the supernatant was measured at 410 nm using an equal volume of phosphate buffer as a blank. The $H_2O_2$ level was determined with an extinction coefficient of 0.28 $mmol^{-1}$ $cm^{-1}$. The MDA level was colorimetrically measured as described below. MDA was extracted by homogenizing 0.3 to 0.5 g adventitious roots with 2 ml 5% trichloroacetic acid, and centrifuged at 10,000×g for 5 min at 20° C. A mixture of 1 ml supernatant with 4 ml 0.5% thiobarbituric acid in 20% trichloroacetic acid was heated in a 95° C. water bath for 30 min and centrifuged for 10 min at 2000×g to remove haziness. Optical density of the supernatant was measured at 532 nm and 600 nm using 1 ml 5% trichloroacetic acid to replace supernatant as a blank. The concentration of MDA was calculated with an extinction coefficient of 155 $mmol^{-1}$ $cm^{-1}$.

Quantification of Total Saikosaponins

The saikosaponins level was measured according to Li et al. (Li X. Q. et al., Biol. Pharm. Bull. 28 (2005) 1736-1742) with some modifications. Freeze-dried adventitious roots were ground into a fine powder and extracted with 70% methanol at a ratio of 10:1 (v/w) at 25° C. with gentle shaking for 24 h. After centrifugation at 10,000×g for 10 min, the supernatant was filtered through a 0.45 μm filter. The amount of total saikosaponins (saikosaponin-a, saikosaponin-c, and saikosaponin-d) in each extract was quantified using a high performance liquid chromatograph (HPLC) (Waters 600 controller autoinjector) with a C18 Inertsil 5 ODS-2 column (4.6 mm×250 mm) and a mobile phase of 45% acetonitrile/55% $H_2O$. The flow rate was 1 ml $min^{-1}$, the injection volume was 20 μl, and the eluent was monitored at 210 nm using a Waters 996 photodiode array detector.

Total Cellular RNA Extraction

Total cellular RNA was extracted as described by Chang et al. (Chang et al., Plant Mol. Biol. (1993) 693-699) with some modifications. Three to five grams of tissue was frozen in liquid nitrogen and ground to a fine powder with mortar and pestle. The powder was added to 15 ml of prewarmed (65° C.) extraction buffer (2%, v/v hexadecyltrimethylammonium bromide (CTAB), 2%, v/v polyvinylpyrrolidinone K 30 (PVP), 100 mM Tris-HCl, pH 8.0, 25 mM EDTA, 2 M NaCl, 0.5 mg $ml^{-1}$ spermidine, 2% β-mercaptoethanol), and mixed completely by vigorous shaking. The mixture was extracted twice with an equal volume of chloroform:isoamyl alcohol (24:1). The RNA was precipitated by adding ¼ volume of cold 10 M LiCl to the aqueous phase and held for 12 to 18 h at −20° C. After centrifugation at 19,800×g at 4° C., the RNA was dissolved in 500 μl sterile DEPC $H_2O$. The resuspended RNA was reextracted with chloroform:isoamyl alcohol (24:1). Three volumes of 100% ethanol and 1/10 volume of 3 M sodium acetate (pH 5.2) were added to the aqueous phase, and the solution was precipitated with liquid nitrogen for 15 min The RNA was spun down at 19,800×g for 30 min at 4° C. and washed with 80% ethanol. The dried pellet was resuspended in sterile DEPC $H_2O$.

Preparation of PCR-Select cDNA Subtraction Library and DNA Sequencing

Three PCR-select cDNA subtraction libraries were constructed with a MeJA-treated sample as tester and control as driver at 13 time points. RNA for construction of libraries I, II and III was prepared from samples at three sets of time points with set I of 5 min, 1, 2, 8 and 24 hours, set II of 2, 4, 6 and 8 days and set III of 2, 3, 4 and 5 weeks, respectively. Within each set, an equivalent amount of RNA from each time point was added to a total of 1.25 mg. Polyadenylated RNA was purified from total cellular RNA using an mRNA Purification Kit (Amersham Biosciences). Total RNA of 1.25 mg was dissolved in 1 ml elution buffer (10 mM Tris-HCl, pH 7.4, 1 mM EDTA) and applied to an oligodT cellulose column. After washing twice with a high-salt buffer (10 mM Tris-HCl, pH 7.4, 1 mM EDTA, 0.5 M NaCl) and three times with a low-salt buffer (10 mM Tris-HCl, pH 7.4, 1 mM EDTA, 0.1 M NaCl), the mRNA was eluted with four aliquots of 0.25 ml elution buffer and used for subtraction with a PCR Select™ cDNA Subtraction Kit (BD Biosciences Clontech). Subtracted cDNA was developed from the mRNA in several steps (first-strand cDNA synthesis, second-strand cDNA synthesis, RsaI digestion, adaptor ligation, first hybridization, second hybridization and PCR amplification). The cDNA was inserted into a pGEM®-T Easy vector (Promega) and transformed into EGOS 101 competent cells (Yeastern Biotech., Taiwan) following the manufacturer's instructions.

Isolated cDNA clones were purified using a Gene-Spin™ Miniprep Purification Kit (Protech). DNA was sequenced via the cycle sequencing reaction method, using a BigDye Terminated Kit (Applied Biosystems Industries) and analyzed with an ABI PRISM® 3100-Avant Genetic Analyzer (Applied Biosystems Industries).

DNA Analysis

After sequencing, ESTs were edited to remove vector sequences and ambiguous data. Sequences shorter than 100 bases were discarded. The ContigExpress program of Vector NTI Suite 6 (InforMax, Inc.) was used to cluster individual ESTs for obtaining uniESTs. Consensus sequences of all the clusters were generated with a minimum length setting of 40 bases. The minimum percentage identity was set at 0.95 to avoid any overlap. The uniESTs were compared to sequences in the AGI protein database using the TAIR WU-BLAST 2.0 algorithm Functional categories for the uniESTs were predicted with the Functional Catalogue Database (FunCatDB) at Munich Information Center for Protein Sequences (MIPS) according to the AGI numbers of the individual uniESTs.

DNA Microarray Fabrication and Hybridization

The cDNA microarray was comprised of 465 uniESTs derived from cDNA subtraction with MeJA treatment. The λ DNA (TX803, Takara) and BkActin (EMBL accession no. AM421809) were used as external and internal controls, respectively. DNA fragments were amplified with nested primers 1 and 2R and purified with a MultiScreen PCR Cleanup Kit (Millipore). The PCR products were present as single bands when examined on agarose gel electrophoresis. Final concentrations were equal to or greater than 100 ng $\mu^{-1}$ in 50% DMSO, as estimated by a TotalLab image analysis system (Phoretix, Newcastle, UK). Qualified DNA fragments were spotted four times as technical replicates at 24 to 26° C. under 60% RH on CMT-GAPS II coated glass slides (Corning) using Cartesian SynQUOD PixSys4500 (Genomic Solutions). After printing, the slides were immobilized by baking at 80° C. for 4 h, and then incubated in a blocking reagent (5-fold SSC, 0.1% SDS, 0.1 mg $ml^{-1}$ BSA and 50% formamide) for 60 min at 42° C. To fix the printed DNA, slides were transferred into isopropanol for 1 min and then dried by centrifugation for 10 min at 90×g. A 500 pg polyA+λ RNA (TX802, Takara) was used as an external control. RNA samples at each time point were labeled (two channels) with cyanine 3 (Cy3; control) and cyanine 5 (Cy5; MeJA-treated) dyes with two biological replicates. Hybridization signals for each feature were scanned using GenePix 4000B and digitized with GenePix 3.0 software (Axon Instruments, Inc.).

Analysis of Microarray Data

The DNA microarray data were imported into GeneSpring 7.2 (Silicon Genetics) for further analyses. Only fluorescent intensities of technical replicated features which had a coefficient of variation less than 0.35, for at least three replicated features, were used for further analyses. The coefficient of variation was calculated by dividing the standard deviation by the mean. Net intensities of both channels were calculated by subtraction of the median fluorescent intensity of the background from the mean fluorescent intensity of each feature. The fluorescent intensity of each clone was divided by its corresponding control, and then normalized with the expression fold of BkActin gene as 1. Fold change was calculated for each gene by dividing the average intensity of MeJA-treated samples by the average intensity of the corresponding control samples.

Clusters of MeJA-induced genes were selected based on filtering with net intensity ≧1000 and fold change ≧2 in at least one of the 13 time points, and then grouped into three sets according to the duration of upregulation; (1) '5 min to 8 h', (2) '1 to 8 days', and (3) '2 to 5 weeks'. A Venn diagram, drawn with GeneSpring 7.2, organized the three sets into seven groups with different expression trends.

Relative Quantification in Real-Time PCR (qRT-PCR)

Each RNA sample of 10 μg in 9 μl sterile DEPC $H_2O$ and 1 μl oligo-d(T)$_{18}$ primer (100 μM) was denatured at 90° C. for 5 min and chilled on ice for 10 min Then 4μ5× reaction buffer (250 mM Tris-HCl, pH 8.0, 375 mM KCl, 15 mM $MgCl_2$), 2 μl 10 mM dNTP, 2 μl 100 mM dithiothreitol (DTT), and 0.5 μl RNasin ribonuclease inhibitor (40 U $\mu l^{-1}$, Promega) were added and incubated at 37° C. for 10 min. After the addition of 1.5 μl Moloney murine leukemia virus (MMLV) reverse transcriptase (200 U $\mu l^{-1}$, Gibco BRL), the reaction was carried out at 37° C. for 90 min, 95° C. for 5 min, then chilled on ice. qRT-PCR reactions were performed with a SYBR Green PCR Master Mix (Applied Biosystems) in a 7500 Real-Time PCR System (Applied Biosystems) using primers designed with Primer Express 2.0 Software (Applied Biosystems). Each reaction was performed in triplicate, and contained 4 μl of a 1:1000 dilution of synthesized cDNA, primers to a final concentration of 100 nM each, 5 μl of the SYBR Green PCR Master mix and sterile deionized $H_2O$ to a total volume of 10 μl. PCR reactions were carried out at 50° C. for 2 min, 95° C. for 10 min, 40 cycles of 95° C. for 15 s and 60° C. for 1 min. The specificity of the amplified products was evaluated by analysis of the dissociation curves generated by the equipment. Non-template controls were prepared to confirm absence of contamination. The ratio between the relative amounts of the target gene and the endogenous control gene, in the qRT-PCR reactions, was determined based on the $2^{-\Delta\Delta Ct}$ method. The target gene expression level was plotted as $\log_{10}$ RQ (RQ=$2^{-\Delta\Delta Ct}$).

Results

MeJA Increased Saikosaponin Production and Decreased Adventitious Root Growth

Total saikosaponins produced in adventitious root of *B. kaoi* were significantly increased by 500 μM (38-fold) or 1000 μM (21-fold) MeJA (P<0.05) 2 weeks after treatment (Table 1). Increasing MeJA concentration from 500 to 1000 μM did not enhance saikosaponin production, thus 500 μM of MeJA was used in further experiments.

Figure 1B:
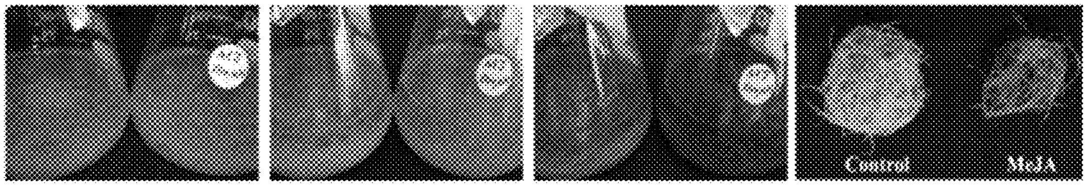
Figure 1C:
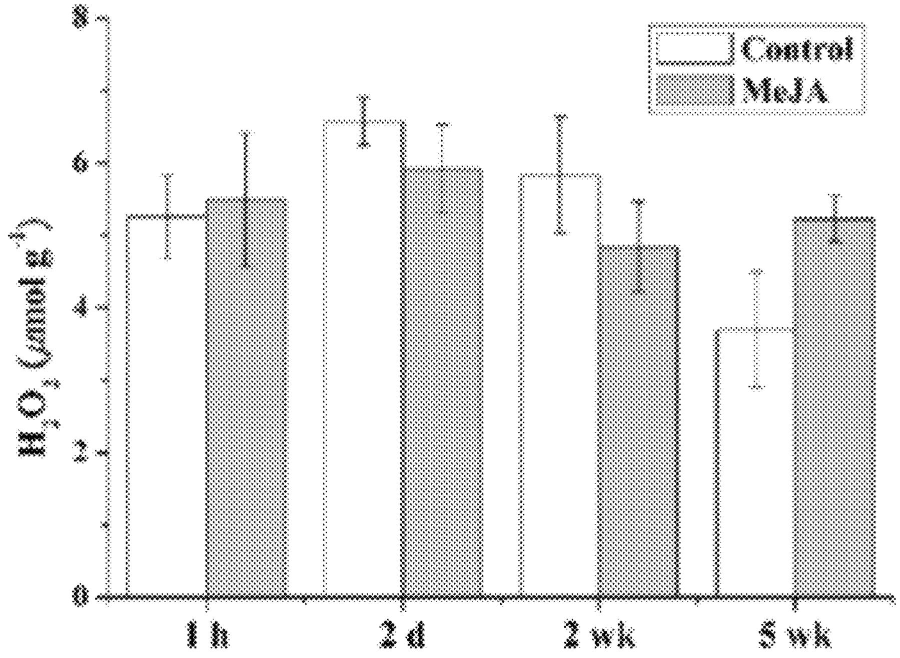
Figure 1D:
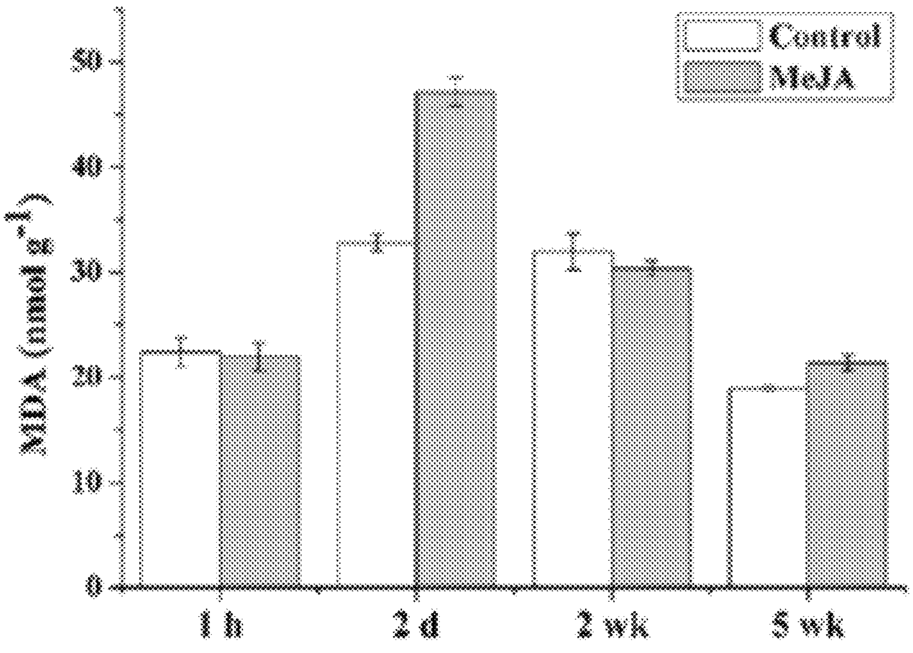

MeJA was applied 4 weeks after nutrient refreshment and the fresh weights of adventitious roots were measured. Growth of *B. kaoi* adventitious roots was retarded 8 days after 500 μM MeJA treatment (FIG. 1A) and the roots displayed marked pigmentation 2 weeks later, as compared to the control (FIG. 1B). The $H_2O_2$ levels in the adventitious roots did not significantly change during the 5 weeks culture, with or without MeJA (FIG. 1C). Although MeJA caused a 1.4-fold increase in the MDA level at 2 days (FIG. 1D), the accumulation of MDA was low (<47 nmol $g^{-1}$) in all treatments during 5 weeks. The low levels of $H_2O_2$ and MDA indicates that the *B. kaoi* adventitious roots were not under detectable oxidative stress.

TABLE 1

Effect of MeJA on saikosaponin production in *B. kaoi* adventitious roots

| MeJA concentration (μM)[a] | Saikosaponin (μg $g^{-1}$ of dry wt)[b] |
|---|---|
| 0 | 1.65 ± 0.52 |
| 500 | 63.60 ± 20.46 |
| 1000 | 39.73 ± 13.25 |

Values are presented as means ± S.E. (n = 3) and are significantly different at P < 0.05 by one-way ANOVA.

[a]Exogenous MeJA was applied to adventitious roots 14 days after subculture.

[b]Total saikosaponin was measured 14 days after MeJA treatment.

PCR-Select cDNA Subtraction Library Construction, Sequencing and Analysis

After MeJA treatment total cellular RNA was extracted from *B. kaoi* adventitious roots at time intervals of 5 min, 1, 2, 8, 24 h for library 1, 2, 4, 6, 8 days for library II and 2, 3, 4, 5 weeks for library III. A total of 834 ESTs with an average size of 275 bp were sequenced, representing 532 uniESTs (437 non-redundant singletons and 95 clusters formed by 397 ESTs). The 532 uniESTs occupy 63.8% of the total ESTs. The cDNA subtraction libraries were not normalized, thus the number of ESTs that correspond to particular MeJA-responsive genes may reflect the relative abundance of the corresponding transcripts and result in a reduction of singletons.

Gene Expression Profiling of MeJA-Treated *B. kaoi* Adventitious Roots

To characterize the underlying molecular events of MeJA signal transduction in *B. kaoi* adventitious roots, we built a small-scale MeJA-responsive microarray platform. Transcripts were analyzed at a series of time points using a total of 532 potential MJ-responsive uniESTs selected from *B. kaoi* adventitious roots. To corroborate the stringency of our analyses, 67 uniESTs were excluded from further data analysis since their transcript levels were under the 2-fold change threshold. Microarray data sets of thirteen time points from 5 min to 5 weeks, and containing two biological replicates, were generated to profile transcripts. At all time points, similar expression trends occurred in each replicate and data reported in this study were from one biological replicate. ESTs without satisfactory PCR fragments or with redundant AGI numbers were removed. The expression data were highly reproducible, with a coefficient of variation less than 0.35 in at least three technical replicates for all time points.

Figure 2:
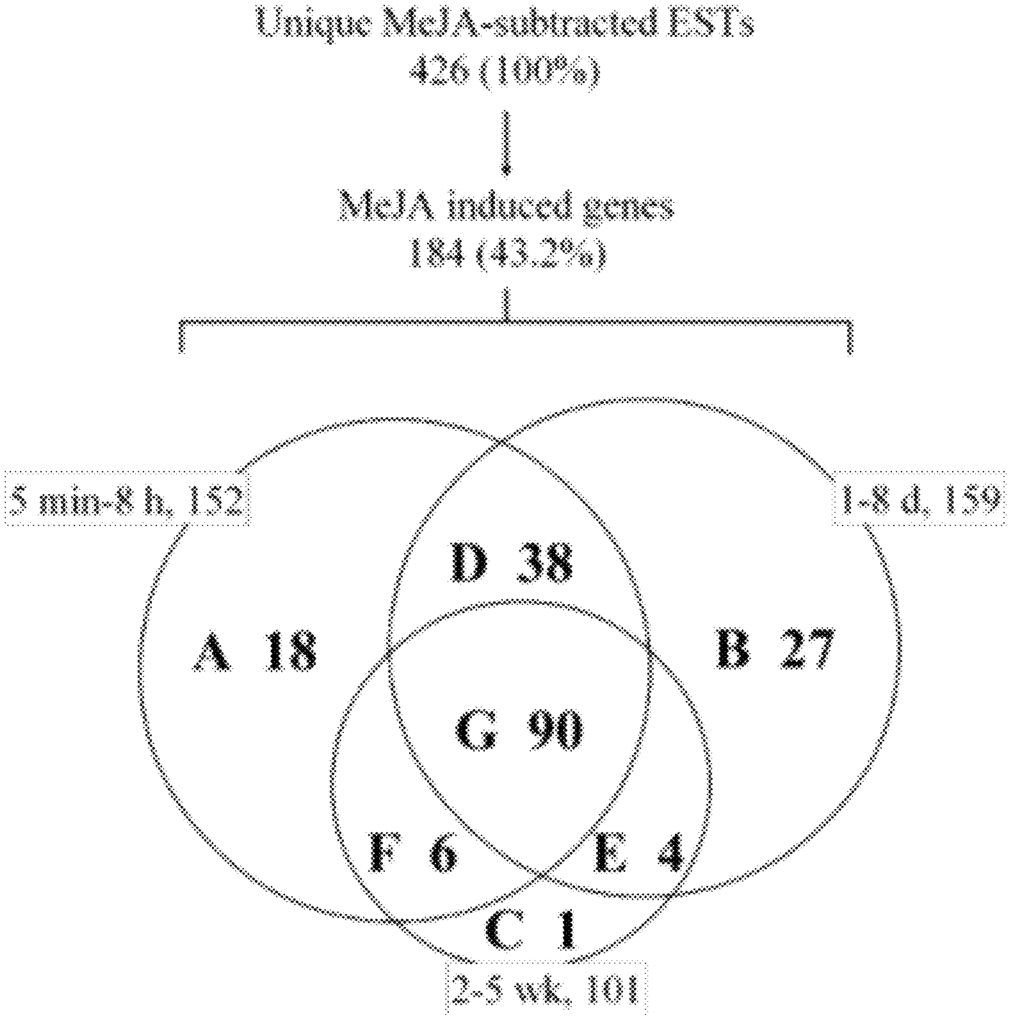
FIG. 2 Venn diagram comparing how sets of '5 min-8 h', '1-8 days' and '2-5 weeks' interact to form seven groups (A-G) based on upregulation kinetics of 184 MeJA-induced genes in *B. kaoi* adventitious roots. Percentages in parentheses were calculated based on the total number of MeJA subtracted uniESTs. Each circle represents a set and the number of MeJA-induced genes in the set is shown in the rectangle.
Figure 3A:
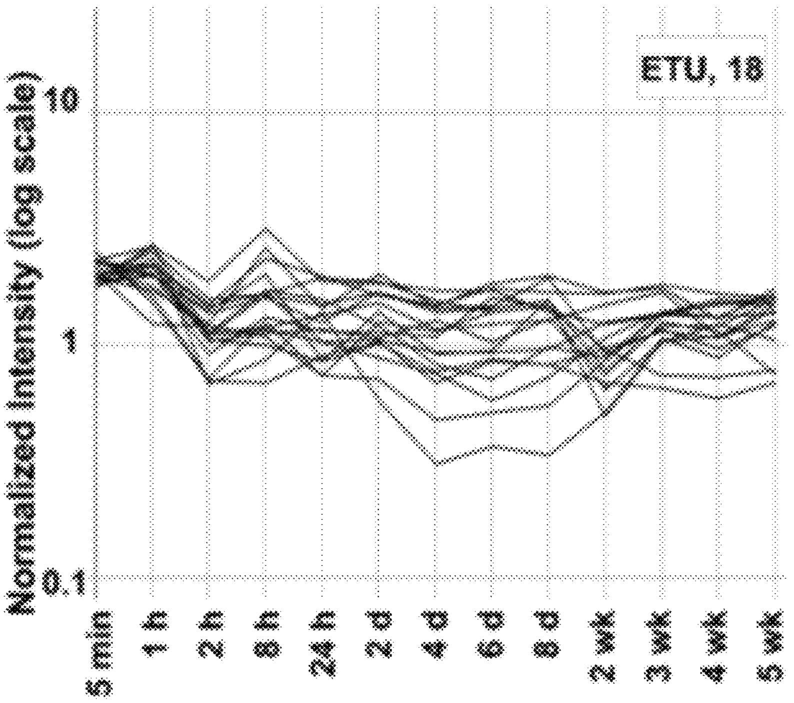
FIG. 3 Dynamic profiling of MeJA-induced gene expression. Gene expression of the seven groups shown in FIG. 2 are graphed in A to G, based on upregulation kinetics. The group and number of MeJA-induced genes in each group are shown in rectangles. The Y-axis is the normalized intensity of log scale, which was calculated as fold change. Fold change of each gene is equal to average intensity of MeJA-treated/average intensity of the corresponding control. ETU, early transiently upregulated; IU, interveningly upregulated; LU, late upregulated; CU-hd/dw/hw/hdw, continually upregulated in more than two durations, h indicates 5 min to 8 h, d indicates 1-8 days, w indicates 2-5 weeks.
Figure 3B:
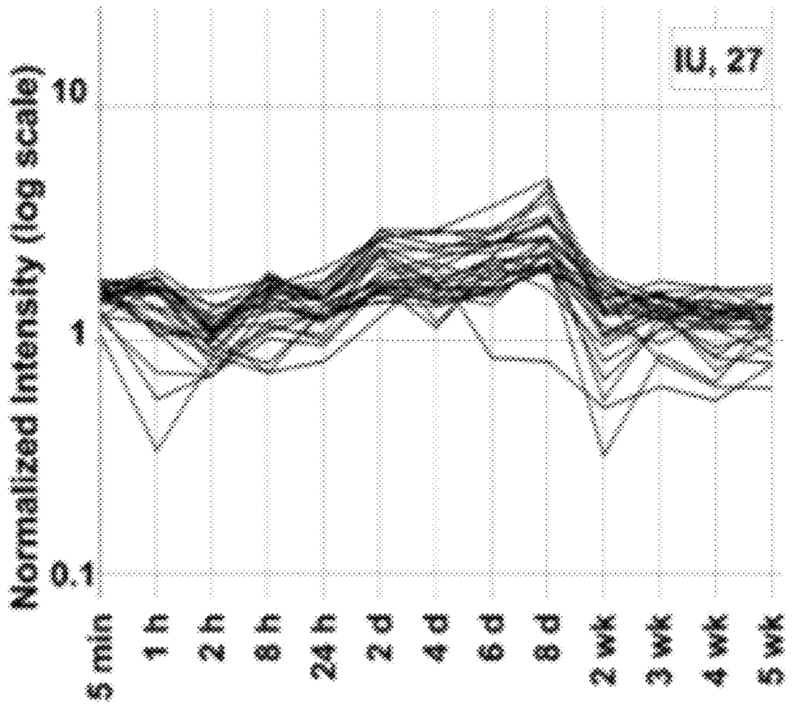
Figure 3C:
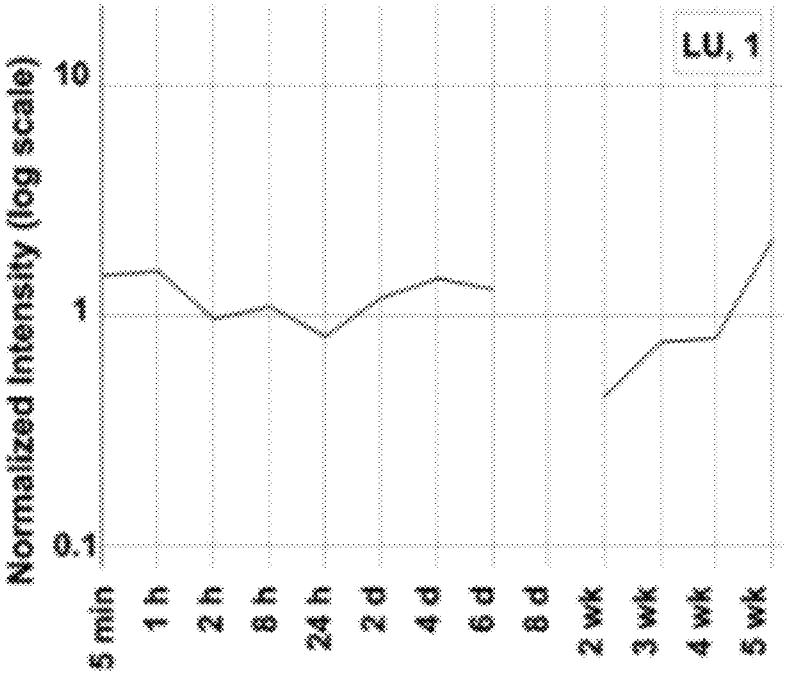
Figure 3D:
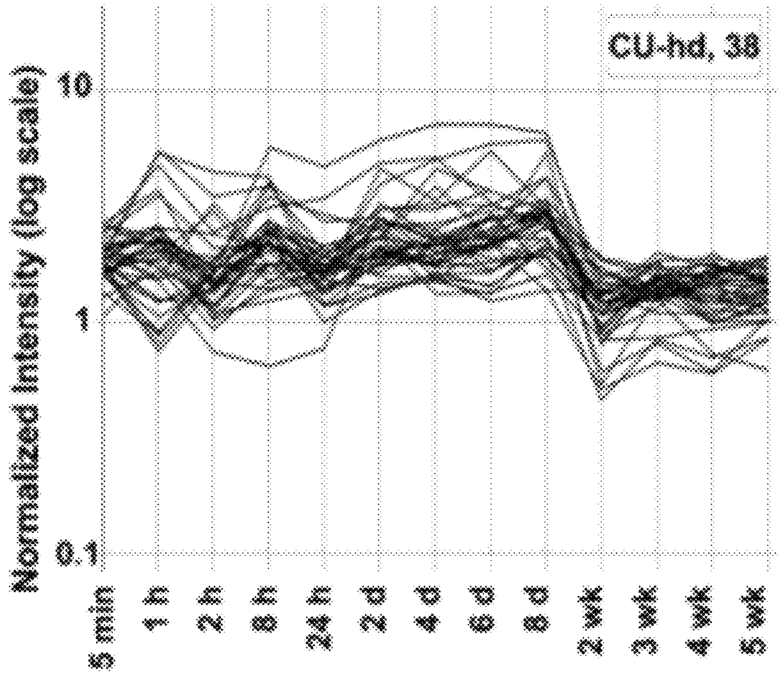
Figure 3E:
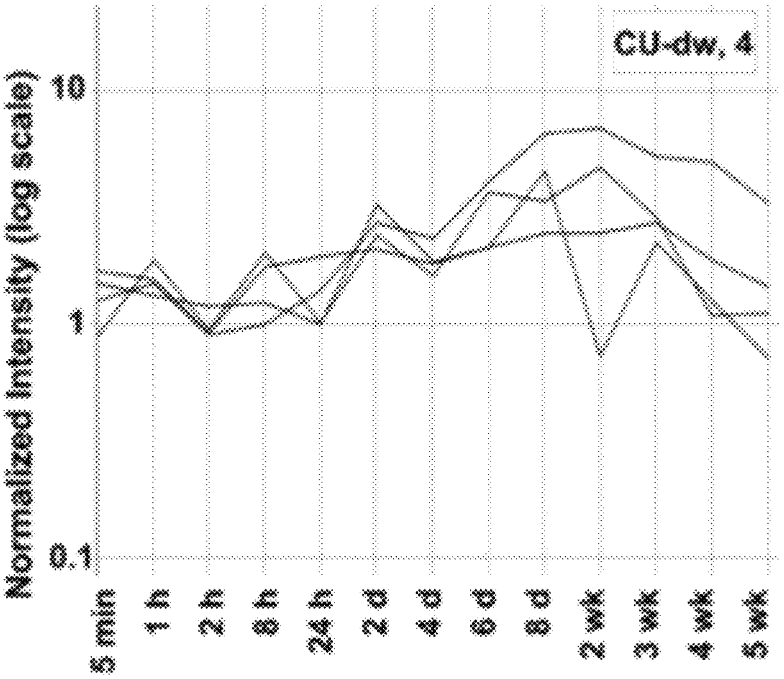
Figure 3F:
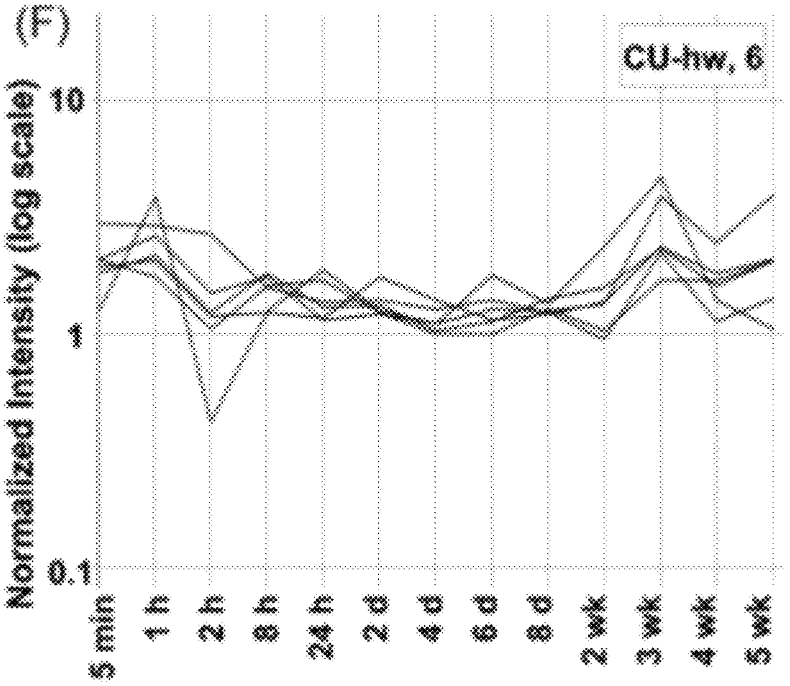
Figure 3G:
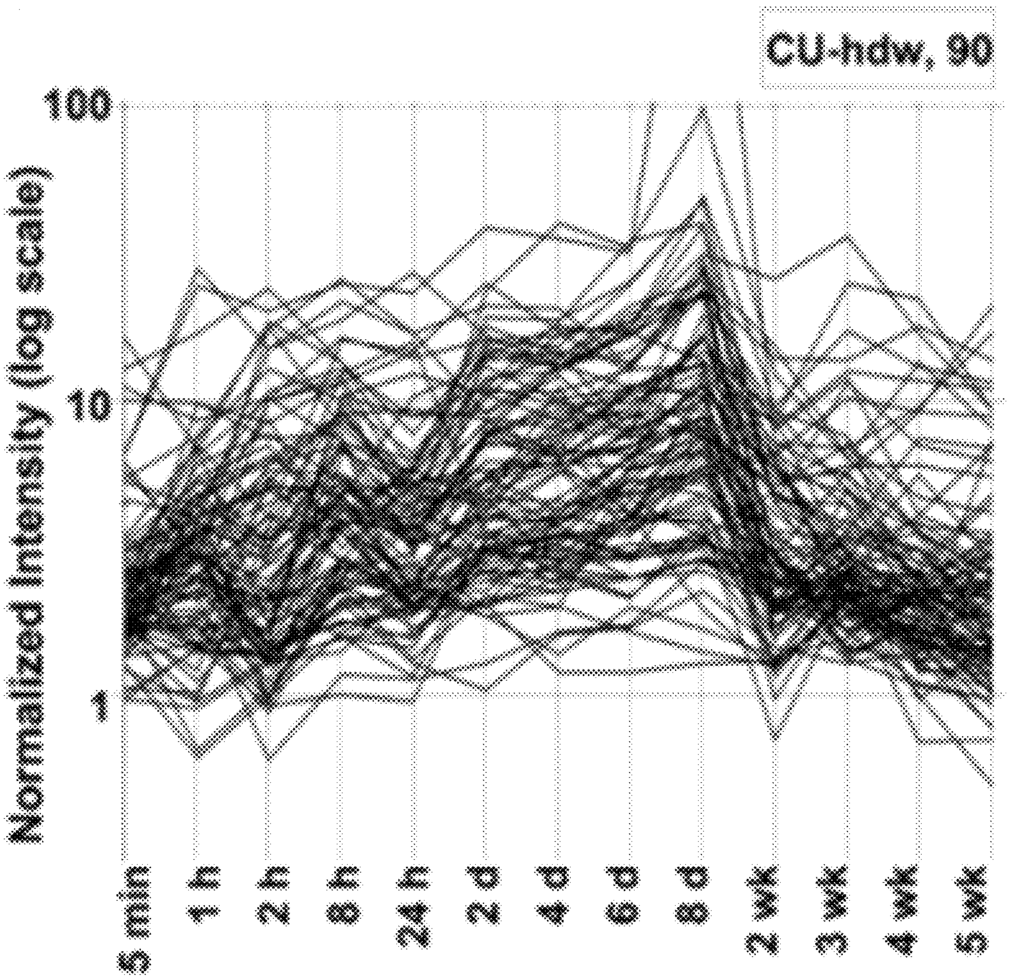

About 87% of the uniESTs positively responded to MeJA treatment at one or more time points. Of the 465 uniESTs, 439 have homologs based on BLASTX hits in the AGI proteins database and the remaining 26 uniESTs did not show significant BLASTX results. Our stringent filtering criteria selected samples with net intensity of Cy5≧1000 and fold change ≧2 at one or more time points. We found 184 genes that conformed to this criterion. GeneSpring 7.2 was used to analyze the gene expression of these 184 genes over three time periods (5 min to 8 h, 1-8 days and 2-5 weeks). Gene set '5 min to 8 h' denotes early responsive genes with more than a 2-fold increase during the period of 5 min to 8 h. Similarly, '1 to 8 days' and '2 to 5 weeks' indicate sets of intermediate response genes and late responsive genes with more than a 2-fold increase in 1 to 8 days and 2 to 5 weeks. These three gene sets were organized into seven groups with different upregulation kinetics under MeJA treatment (FIG. 2). Genes with transcript levels that increased only at 5 min to 8 h, 1 to 8 days, and 2 to 5 weeks were designated as early transient upregulated (ETU), intermediate upregulated (IU) and late upregulated (LU), respectively. Genes with upregulated expression in more than two periods were grouped as continually upregulated (CU), including 5 min to 8 days (CU-hd), 1 day to 5 weeks (CU-dw), 5 min to 8 h and 2 to 5 weeks (CU-hw) and 5 min to 5 weeks (CU-hdw). The 'ETU' set contains 18 genes, including those that encode a calmodulin, a phosphoinositide phosphatase protein and a Ras-related GTP binding protein (FIG. 3A). The 'IU' set contains 27 genes including those that encode a 14-3-3 protein, 2 P450s, a Ring finger protein, a sucrose synthase, a vacuolar ATPase and a WRKY transcription factor (FIG. 3B). 'LU' contains 1 gene of unknown function (FIG. 3C). The 'CU-hd' set is comprised of 38 genes including those that encode a disease resistance protein, an F-box protein and a 26S proteasome regulatory subunit (FIG. 3D). The 'CU-dw' set is comprised of 4 genes, including that encode a plant defense protein (FIG. 3E). The 'CU-hw' set has 6 genes, including those that encode an omega-6 fatty acid desaturase and other proteins of unknown function (FIG. 3F). The most expansive expression pattern is the 'CUhdw' set that describes the genes upregulated spreading from hours to weeks, with the most significant upregulation in 5 min to 8 days (FIG. 3G). This group has 90 genes, including those that encode a 1-aminocyclopropane-1-carboxylate oxidase (ACO), an auxin-responsive protein, a $C_2H_2$ type zinc finger protein, 2 ethylene-responsive factors (ERF), 3 glutathione-S-transferases (GST), a lipoxygenase (LOX) and a MYB transcription factor. Among the 184 MeJA induced genes, 172 genes identified by AGI codes were grouped into functional categories using the MIPS database and the metabolism-related genes formed the largest category (11.06%, Table 2).

TABLE 2

Functional categorization of MeJA-regulated genes

| Functional category | 165 genes (%)[a] |
|---|---|
| Metabolism | 11.06 |
| Energy | 2.40 |
| Cell cycle and DNA processing | 0.48 |
| Transcription | 3.37 |
| Protein synthesis | 2.88 |
| Protein fate (folding, modification, and destination) | 1.44 |
| Protein with binding function or cofactor requirement | 3.37 |
| Cellular transport, transport facilitation and transport routes | 2.88 |
| Cellular communication/signal transduction mechanism | 0.96 |
| Cell rescue, defense and virulence | 2.88 |
| Interaction with the cellular environment | 0.48 |
| Interaction with the environment (systemic) | 0.96 |
| Cell fate | 0.48 |
| Development (systemic) | 0.48 |
| Biogenesis of cellular components | 1.92 |
| Subcellular localization | 7.21 |
| Tissue localization | 0.48 |

TABLE 2-continued

Functional categorization of MeJA-regulated genes

| Functional category | 165 genes (%)[a] |
|---|---|
| Organ localization | 0.96 |
| No clear classification/unclassified | 55.29 |

[a]One hundred seventy two out of 184 MeJA upregulated genes have homologous *Arabidopsis* genes. The 172 genes were categorized with an *Arabidopsis* MIPS database containing 26642 annotated genes. Seven were not found in the database.

Verification of Microarray Data with qRT-PCR

Real-time quantitative RT-PCR (qRT-PCR) was applied to validate the microarray data of the 35 uniESTs that had a fold change >3 at any time point (CU-hdw) and one EST in 'CU-hd' set. We deposited the sequences in EMBL Nucleotide Sequence Database (accession nos. AM409278 to AM409313 and AM421810 to AM421813). A BkActin gene homogeneously expressed with equivalent transcript levels in all samples was used for data normalization. Setting a criterion of fold induction >3 at any time point (CU-hdw), 70% of genes examined with qRT-PCR showed a similar expression profile with that of microarray results. Potential functionality of genes described below was attributed based on homology to genes of known function in other organisms.

MeJA Increased Transcripts of Enzymes Involved in Saikosaponin Biosynthesis

Figure 4A:
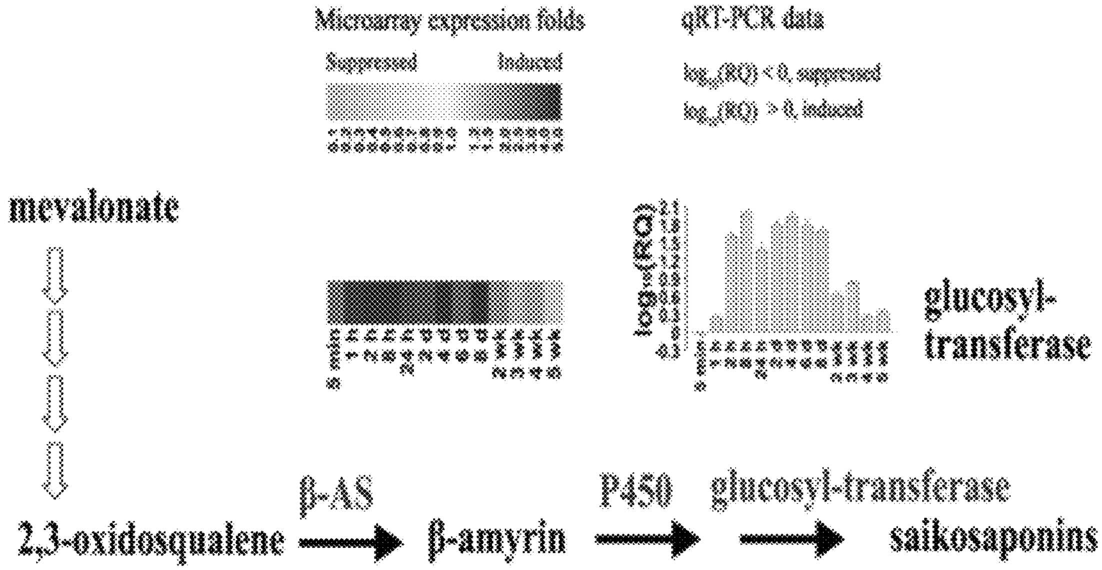
FIG. 4 Gene regulation by MeJA of members in saikosaponin biosynthesis (A), the core phenylpropanoid pathway (B) and octadecanoid pathway (C). Pathway steps are indicated by arrows. The intermediate products, enzymes and associated genes are shown. Microarray expression data are shown in heatmap format. Data from qRT-PCR indicate fold induction ($\log_{10}$ scale). Error bars represent S.D. of the induction values.

Saikosaponins are synthesized via the isoprenoid pathway by cyclization of 2,3-oxidosqulene to produce oleanane β-amyrin) or dammarane triterpenoid skeleton and the triterpenoid backbone is modified by P450 and glycosyltransferases. The proteins encoded by these genes may contribute to saikosaponin production. Although the transcript level of a *B. kaoi* β-amyrin synthase gene (β-AS) (EMBL accession no. AM421813) was increased only 2-fold by MeJA, the *B. kaoi* gene encoding UDP-glucosyltransferase (EMBL accession no. AM409293) involved in saikosaponin biosynthesis was markedly induced (98-fold) by MeJA at 8 h (FIG. 4A). In addition, two BkP450 genes (EMBL accession nos. AM421810 and AM421812) also showed a 2-fold increase in our microarray analysis.

MeJA Increased Transcripts of Enzymes Involved in Amino Acid Biosynthesis

MeJA has been reported to induce genes involved in primary metabolism in *Arabidopsis*, leading to the formation of tryptophan derivatives, which are terpenoid idole alkaloid precursors. In our study, MeJA treatment profoundly affected expression of the gene coding for prephenate dehydratase (EMBL accession no. AM409309), which is a regulatory enzyme catalyzing the conversion of prephenate to phenylpyruvate in phenylalanine biosynthesis. The level of prephenate dehydratase transcripts was induced 7-fold at 2 h and 27-fold at 6 days by MeJA. MeJA affected non-aromatic amino acids biosynthesis as well. A gene encoding pyruvate kinase (EMBL accession no. AM409311) was induced 3-fold at 8 h and 9-fold at 4 days by MeJA. Pyruvate kinase serves as a key enzyme in the conversion of pyruvate, which is a major precursor for alanine, valine and leucine.

MeJA Increased Transcripts of PAL and C4H in Phenylpropanoid Biosynthesis

Figure 4B:
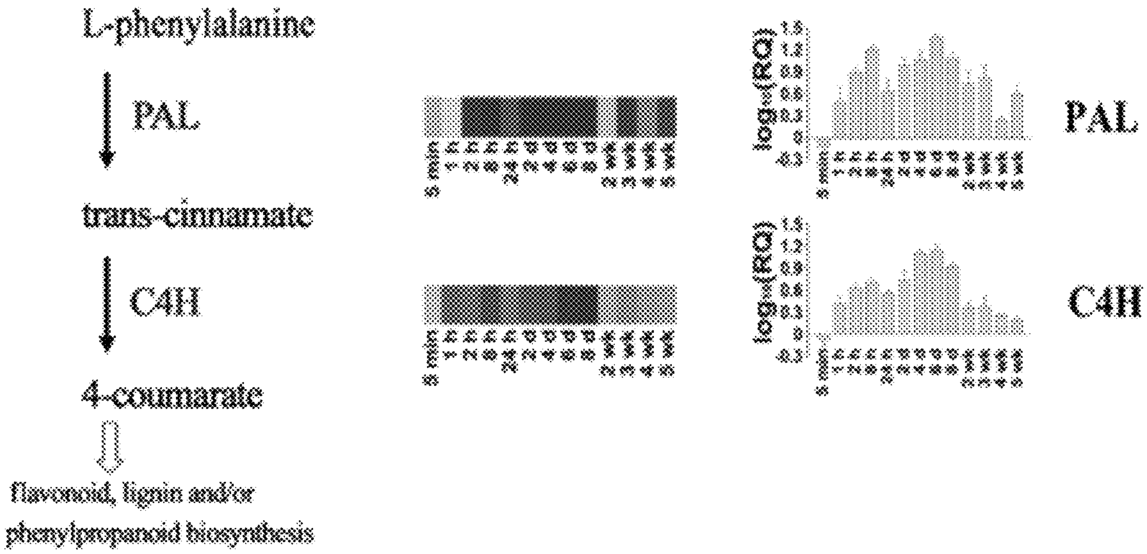

MeJA induced genes encoding proteins involved in the initial metabolic pathway of phenylpropanoid biosynthesis, including phenylalanine ammonia-lyase (PAL) (EMBL accession no. AM409299) and cinnamic acid 4-hydroxylase (C4H) (EMBL accession no. AM409304) (FIG. 4B). The level of PAL transcripts was induced 3-fold in cell suspension cultures of *Medicago truncatula* after exposure to 5 μM MeJA for 2 h. Our qRT-PCR results showed that the level of *B. kaoi* PAL transcripts in adventitious roots was increased 3-fold at 1 h and 23-fold at 6 days by 500 μM MeJA; the C4H transcripts showed similar pattern.

MeJA Increased Transcripts of Enzymes Involved in Jasmonic Acid Biosynthesis

Figure 4C:
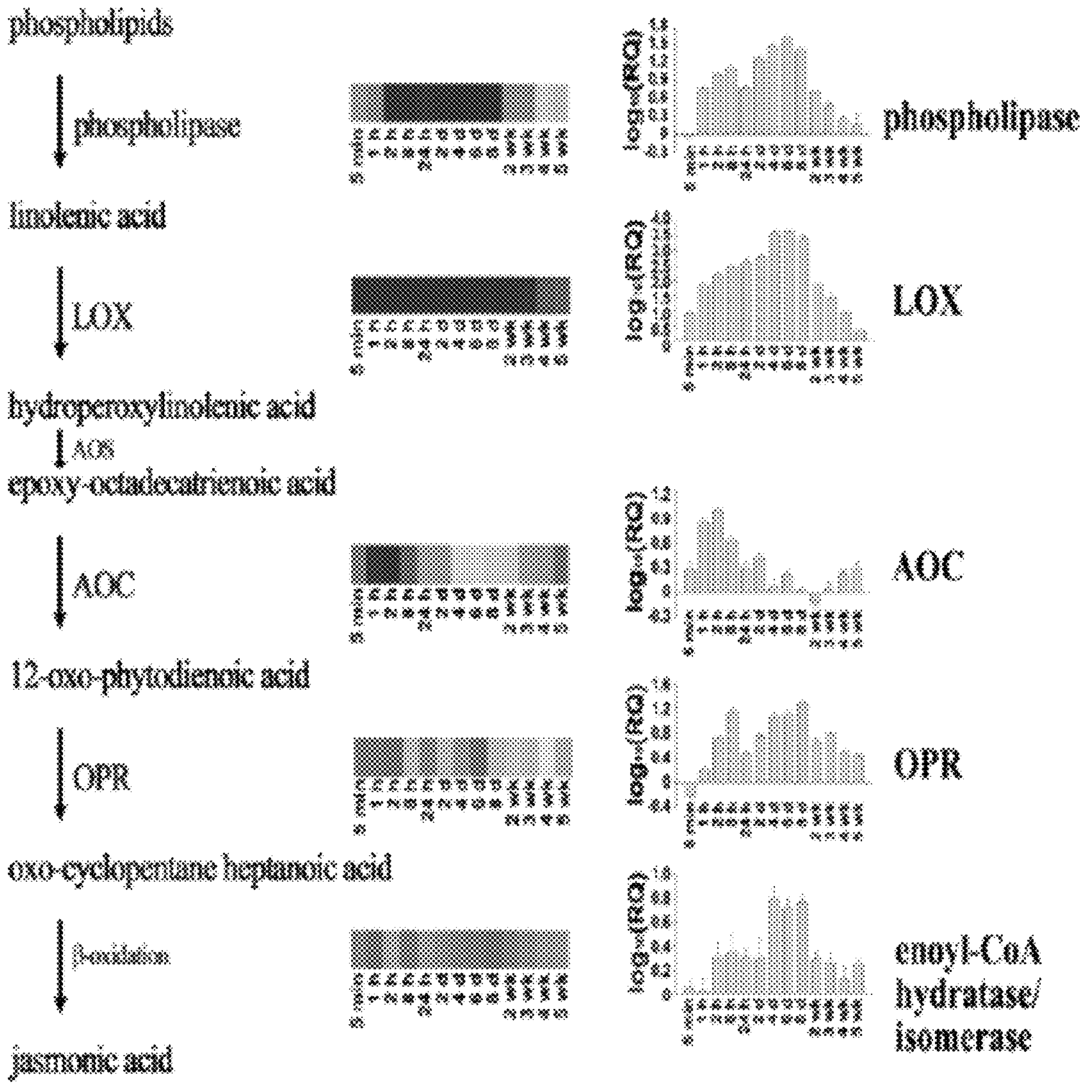

Consistent with a previous report (Sasaki Y., et al., DNA Res. 44 (2005) 653-668), self-activation of JA was indicated by the activation of JA biosynthesis genes coding for the phospholipase D alpha 1 (EMBL accession no. AM409303), LOX (EMBL accession no. AM409291), allene oxide cyclase (AOC) (EMBL accession no. AM409312) and 12-oxophytodienoate reductase 2 (OPR2) (EMBL accession no. AM409310) (FIG. 4C). Previous studies showed that the LOX1 (Melan M. A. et al., Plant Physiol. 101 (1993) 441-450) and AOC genes were MeJA-responsive, but phospholipase D alpha 1 has never been reported to be upregulated by JA, although it is induced by cold. The level of *B. kaoi* phospholipase D alpha 1 transcripts was induced 6-fold at 1 h and 44-fold at 6 days. The LOX transcript was markedly induced at all time points, with a very high level of 4404-fold at 6 days. The BkAOC mRNA level was induced 9-fold at 2 h. MeJA induced the expression level of OPR25-fold at 2 h and 19-fold at 8 days, similar to that of *Arabidopsis* OPR3. Downstream of 12-oxo-phytodienoic acid reduction, the octadecanoid pathway includes three rounds of b-oxidation. A *B. kaoi* gene coding for enoyl-CoA hydratase (EMBL accession no. AM409286) that functions in fatty acid β-oxidation was induced 6-fold by MeJA primarily in 4-8 days.

MeJA Increased mRNA Levels of Transcription Factors

Figure 5A:
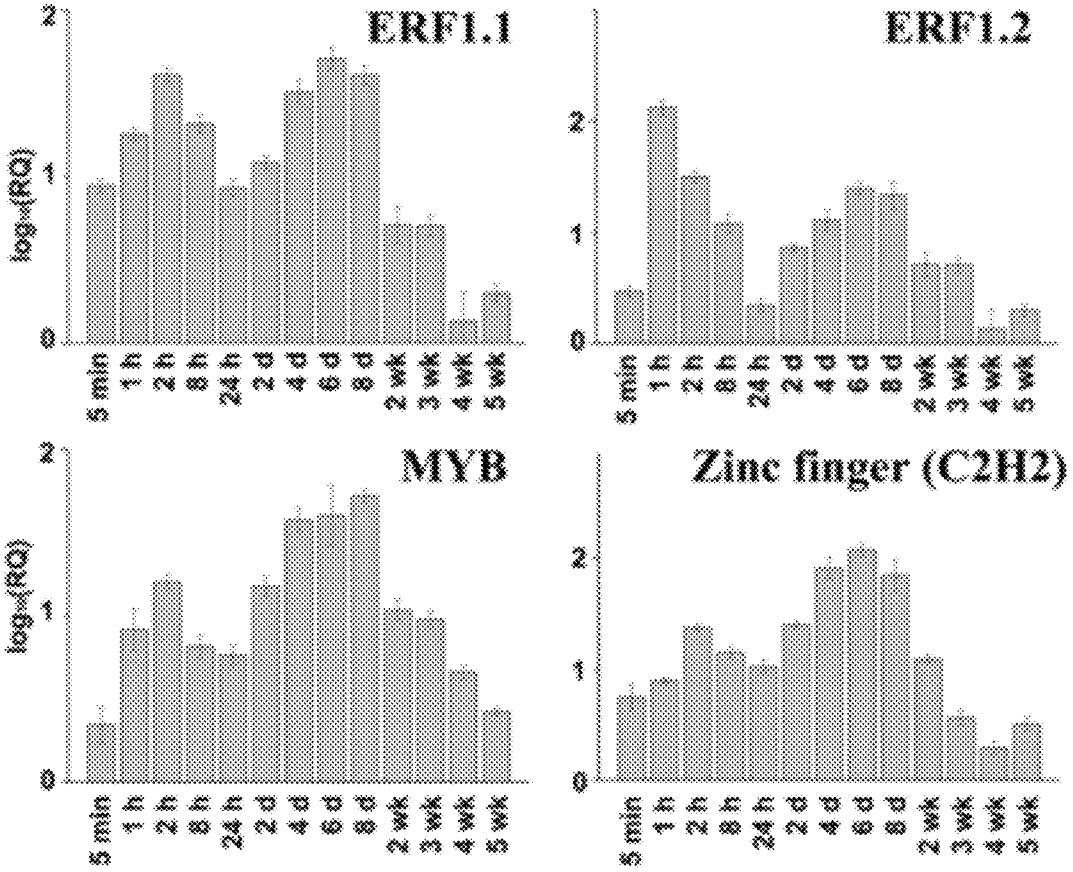
FIG. 5 Transcript programming of genes upregulated by MeJA. qRT-PCR was performed to validate the microarray data showing the fold induction ($\log_{10}$ scale) at 13 time points for genes coding for ERF1, MYB and Zinc finger ($C_2H_2$) transcriptional factors (A), PIN, IAA-amido synthase, IAA-amino acid hydrolase and ACO (B), plant defensin, basic endochitinase and glycosyl hydrolase family 18 (C), trypsin protease inhibitor, protease inhibitor and serine protease inhibitor (D), GST and peroxidase (E). Error bars represent S.D. of the induction values.

Transcription levels of genes encoding 4 transcription factors were induced 5 min after MeJA treatment and the induction continued to 3 weeks (FIG. 5A). MeJA increased transcripts of BkERF1.1 (EMBL accession no. AM409278) 41-fold at 2 h and that of BkERF1.2 (EMBL accession no. AM409280) 133-fold at 1 h. The activation of ERFs may lead to the expression of a subset of defense genes. Transcripts of a MYB gene (EMBL accession no. AM409302) exhibited a 53-fold increase by MeJA at 8 days. Similarly, transcripts of a zinc finger $C_2H_2$ type gene (EMBL accession no. AM409288) were induced 118-fold at 6 days.

MeJA Mediates Auxin Homeostasis and Signaling Pathway of Other Phytohormones

Figure 5B:
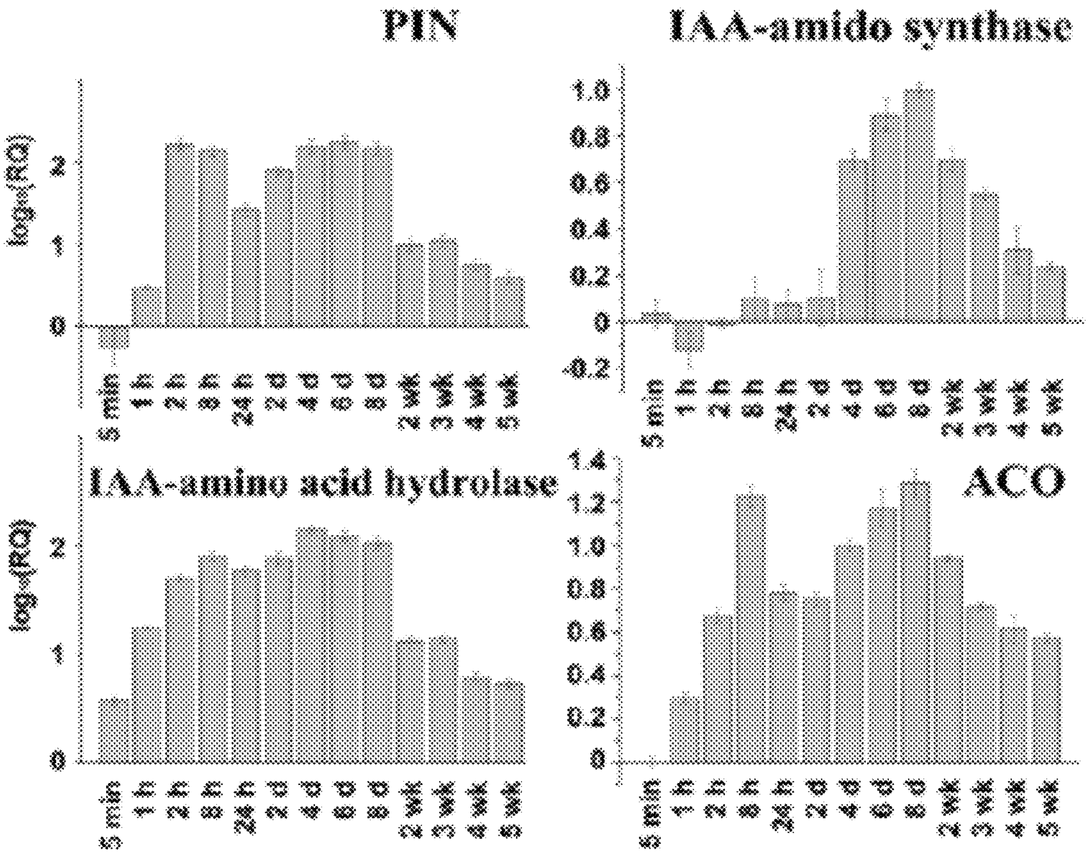

Expressions of genes encoding the auxin efflux carrier (PIN) (EMBL accession no. AM409287) and the IAA-amino acid hydrolase 6 (EMBL accession no. AM409294) were noticeably induced by MeJA. The level of PIN transcripts was increased 166-fold at 2 h and 178-fold at 6 days. Transcripts of IAA-amino acid hydrolase were increased 50-fold at 2 h and 139-fold at 4 days. PIN facilitates IAA distribution and IAA-amino acid hydrolase cleaves the amide bond between IAA and the conjugated amino acid to release active IAA. The gene encoding IAA-amido synthase (EMBL accession no. AM409281) that conjugates excess IAA to amino acids was induced to 5-fold at 4 days and 10-fold at 8 days (FIG. 5B). The coordination of PIN, IAA-amino acid hydrolase and IAA-amido synthase may maintain auxin homeostasis in the adventitious roots.

Both ABA and ethylene are plant stress hormones with growth-inhibiting activities. A gene coding for the last enzyme of ethylene biosynthesis, ACO (EMBL accession no. AM409282), was induced 5-fold at 2 h and 19-fold at 8 days by MeJA (FIG. 5B). Short-chain dehydrogenase/reductase (SDR) gene family plays a unique and specific role in the ABA biosynthesis pathway. Transcripts of a BkSDR (EMBL accession no. AM409290) were increased 4-fold at 6 days. *Arabidopsis* SDR1 is sufficient for the multistep conversion of plastid- and carotenoid-derived xanthoxin to abscisic aldehyde in the cytosol. The products of these two genes may have slightly induced ethylene and ABA and thus retained the growth of adventitious roots (FIG. 1A).

MeJA Increased Expression of Defense Gene Transcripts

Figure 5C:
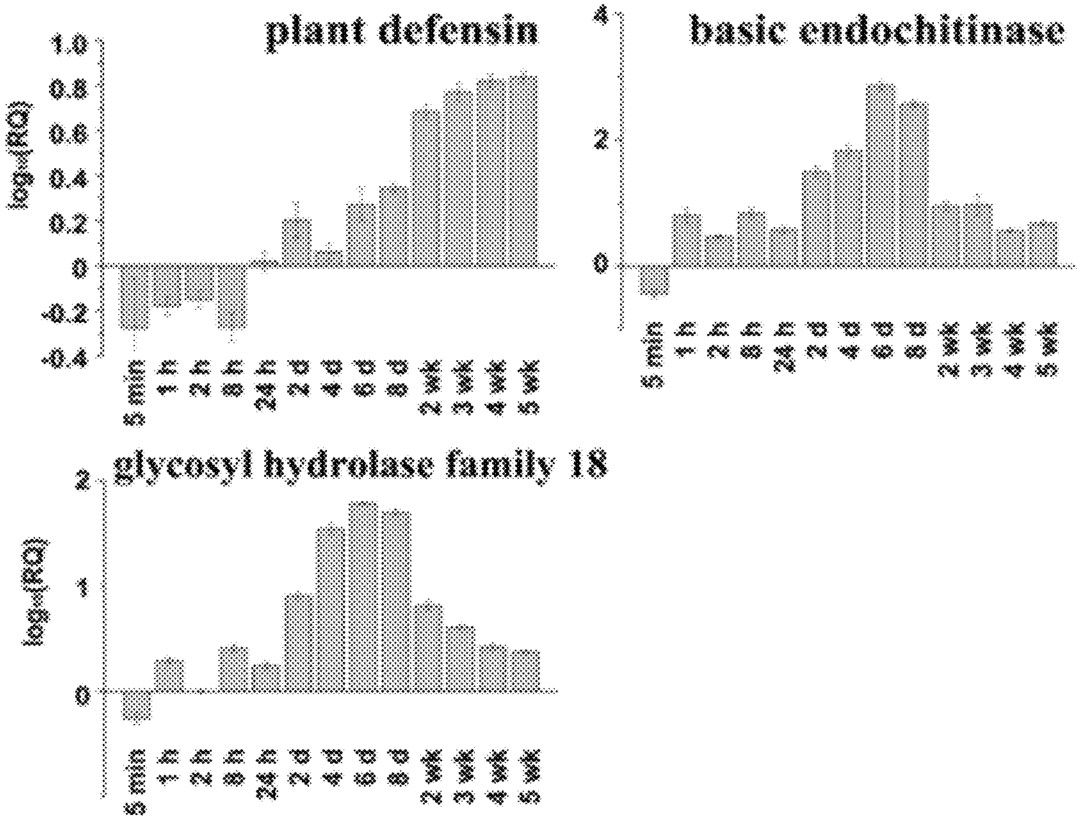
Figure 5D:
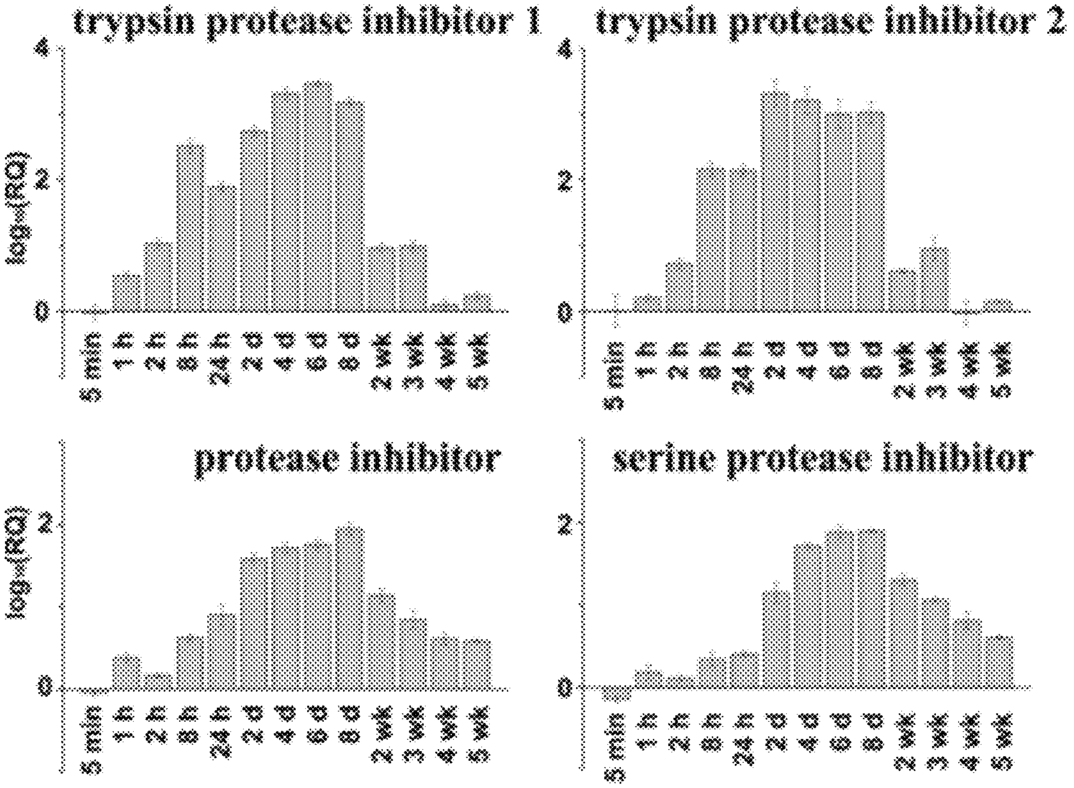

The defense response genes encoding basic endochitinase (EMBL accession no. AM409300) and glycosyl hydrolase family 18 protein (EMBL accession no. AM409313) were induced by MeJA 726-fold and 61-fold at 6 days, respectively. Transcripts of a plant defensin (EMBL accession no. AM409284) were increased 5-fold after 2 weeks (FIG. 5C). MeJA also induced 4 protease inhibitor genes. Transcripts of a protease inhibitor (EMBL accession no. AM409279) were increased 4-fold at 8 h and 90-fold at 8 days. The mRNA level of a serine protease inhibitor (EMBL accession no. AM409301) was increased 3-fold at 24 h and 81-fold at 8 days. In addition, 2 genes encoding trypsin protease inhibitors (EMBL accession nos. AM409305 and AM409295) were dramatically induced by MeJA. Transcripts of AM409305 were increase 4-fold at 1 h and 2944-fold at 6 days. Similarly, transcripts of AM409295 were increased 5-fold at 2 h and 2051-fold at 2 days (FIG. 5D). The activation of these genes may contribute to plant innate immune system.

MeJA Increased Transcripts of Detoxification Enzymes

Figure 5E:
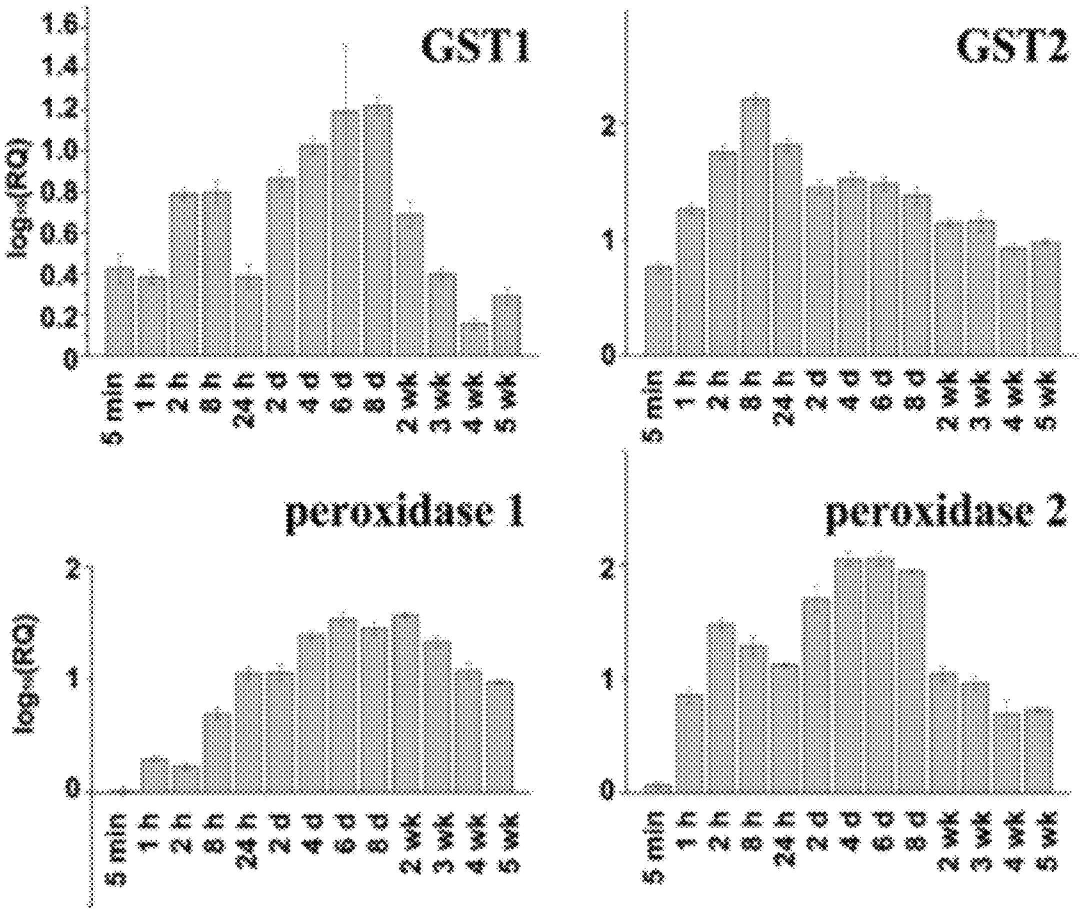

Four genes encoding detoxification enzymes were induced by MeJA at almost all time points (FIG. 5E). Transcripts of the BkGST2 (EMBL accession no. AM409289) were activated 6-fold 5 min after MeJA application and increased 161-fold at 8 h. Transcripts of the BkGST1 (EMBL accession no. AM409308) were increased 3-fold at 5 min and 17-fold at 8 days. Two peroxidase genes (EMBL accession nos. AM409296 and AM409285) were activated sequentially. Transcripts of AM409296 were increased 7-fold at 1 h and 114-fold at 6 days; that of AM409285 were increased 5-fold at 8 h and 37-fold at 2 weeks. Their coding proteins may play roles in the removal of $H_2O_2$ and oxidation of toxic reductants.

Example 2

Materials and Methods

Cloning the Full Gene Length of *B. kaoi* BkERFs

The complete BkERF genes were obtained using isolated mRNA and the rapid of complementary DNA (rapid amplification of cDNA end, RACE) technology based on the three PCR-selected cDNA substration libraries. The full length of cDNA was obtained from 3 μg of the MeJA-treated nucleic acid samples using 5'-end and 3'-end of rapid multiplication according to the BD SMART RACE (Clontech, Japan) manual. Big Dye Terminated reagent kit (Applied Biosystems) and ABI PRISM® 3100 Genetic Analyzer (Applied Biosystems) were used to sequence DNA. Sequence was compared and analyzed using the Basic Local Alignment Search Tool (BLAST) program of National center of Biotechnology (NCBI). The BkERF1 gene contains open reading frame (ORF) of 633 bp, which encodes 210 amino acids. BkERF2.1 gene contains ORF of 693 bp, which encodes 230 amino acids, and BkERF2.2 gene contains ORF of 702 bp, encoding 233 amino acids.

*Arabidopsis* Stable Expression of BkERFs Genes

The coding region of BkERFs was cloned into the multiple cloning site of the binary vector pMON530 under the control of the CaMV 35S promoter and the nopaline synthase termination sequences. The resulting vector was introduced into the *Agrobacterium tumefaciens* strain GV3101, which was introduced into *Arabidopsis* (wild-type Columbia) using

*Agrobacterium tumefaciens*-mediated transformation following the floral dip method (Clough S J et al., Plant J. 16 (1998) 735-743). *Arabidopsis* seed from transformed plants (T0) were harvested and sowed on MS medium (Sigma Chemical Co.) containing kanamycin (Kan) at 50 μg/ml (Sigma Chemical Co.). Primary transformations (T1) were selected and self pollinated in the greenhouse. The progenies of these primary transformants were observed on selective medium and 3:1 (Kan-resistant/Kan-susceptible) segregating lines were selected and transformed to a greenhouse for self pollination. Progenies (T2) of the individual T1 plants were planted on selective medium and those that showed 100% resistance to Kan were selected (homozygous lines). The transgenic *Arabidopsis* plants were grown in soil at 22° C. and T3 plants were confirmed and used for analysis.

Protein Quantity and Gel Eletrophoresis Experiment

Protein quantity was tested with the absorbance of the standard protein concentration curve. The standard protein concentrations were 1.25, 2.5, 5, 10, 15, 20 and 25 μg/ml bovine serum albumin (bovine serum albumin, BSA; Sigma Chemical Co.). Each bovine serum albumin standard of 800 μl was mixed evenly with 200 μl Bio-Rad protein analysis reagent and using spectrophotometer (Beckman, Fullerton, Calif., USA) to test the absorbance of each sample with 595 nm.

Protein was mixed with sample buffer and heated to 95° C. 5 min for inactivation. The sample buffer contained: 100 nM 3-(hydroxymethyl)-amino methane hydrochloride, pH 6.8, 200 mM dithiothreitol (DTT), 4% sodium dodecyl sodium, 0.2% bromophenol blue, and 20% glycerol. The sample was injected into 7.5% SDS-PAGE. 20 mA was used initially to concentrate the protein on the stacking gel, and then 40 mA was used of current experiments. The gel was stained using Coomassie brilliant blue staining buffer for at least one hour of reaction time. The Coomassie brilliant blue contained: 0.125% Coomassie brilliant blue, 50% methanol, and 10% glacial acetic acid. The gel was placed into destaining buffer I (40% methanol and 10% glacial acetic acid) for 1 h and then placed into destaining buffer II (7% methanol and 5% glacial acetic acid) for another one hour to destain.

Total Cellular RNA Extraction

Total cellular RNA was extracted as described by Chang et al. (Chang et al., Plant Mol. Biol. 11 (1993) 693-699) with some modifications. Three to five grams of tissue was frozen in liquid nitrogen and ground to a fine powder with mortar and pestle. The powder was added to 15 ml of prewarmed (65° C.) extraction buffer (2%, v/v hexadecyltrimethylammonium bromide (CTAB), 2%, v/v polyvinylpyrrolidinone K 30 (PVP), 100 mM Tris-HCl, pH 8.0, 25 mM EDTA, 2 M NaCl, 0.5 mg $ml^{-1}$ spermidine, 2% 3-mercaptoethanol), and mixed completely by vigorous shaking. The mixture was extracted twice with an equal volume of chloroform:isoamyl alcohol (24:1). The RNA was precipitated by adding ¼ volume of cold 10 M LiCl to the aqueous phase and held for 12 to 18 h at −20° C. After centrifugation at 19,800×g at 4° C., the RNA was dissolved in 500 μl sterile DEPC $H_2O$. The resuspended RNA was reextracted with chloroform:isoamyl:alcohol (24:1). Three volumes of 100% ethanol and 1/10 volume of 3 M sodium acetate (pH 5.2) were added to the aqueous phase, and the solution was precipitated with liquid nitrogen for 15 min The RNA was spun down at 19,800×g for 30 min at 4° C. and washed with 80% ethanol. The dried pellet was resuspended in sterile DEPC $H_2O$.

Relative Quantification in Real-Time PCR (qRT-PCR)

Each RNA sample of 10 μg in 9 μl sterile DEPC $H_2O$ and 1 μl oligo-$d(T)_{18}$ primer (100 μM) was denatured at 90° C. for 5 min and chilled on ice for 10 min Then 4 μl 5× reaction buffer (250 mM Tris-HCl, pH 8.0, 375 mM KCl, 15 mM $MgCl_2$), 2 μl 10 mM dNTP, 2 μl 100 mM dithiothreitol (DTT), and 0.5 μl RNasin ribonuclease inhibitor (40 U $\mu l^{-1}$, Promega) were added and incubated at 37° C. for 10 min After the addition of 1.5 μl Moloney murine leukemia virus (MMLV) reverse transcriptase (200 U $\mu l^{-1}$, Gibco BRL), the reaction was carried out at 37° C. for 90 min, 95° C. for 5 min, then chilled on ice. qRT-PCR reactions were performed with a SYBR Green PCR Master Mix (Applied Biosystems) in a 7500 Real-Time PCR System (Applied Biosystems) using primers designed with Primer Express 2.0 Software (Applied Biosystems). Each reaction was performed in triplicate, and contained 4 μl of a 1:1000 dilution of synthesized cDNA, primers to a final concentration of 100 nM each, 5 μl of the SYBR Green PCR Master mix and sterile deionized $H_2O$ to a total volume of 10 μl. PCR reactions were carried out at 50° C. for 2 min, 95° C. for 10 min, 40 cycles of 95° C. for 15 s and 60° C. for 1 min The specificity of the amplified products was evaluated by analysis of the dissociation curves generated by the equipment. Non-template controls were prepared to confirm absence of contamination. The ratio between the relative amounts of the target gene and the endogenous control gene, in the qRT-PCR reactions, was determined based on the $2^{-\Delta\Delta Ct}$ method. The target gene expression level was plotted as $\log_{10}$ RQ ($RQ=2^{-\Delta\Delta Ct}$).

*B. kaoi* Cells Overexpress BkERFs Genes

Figure 6:
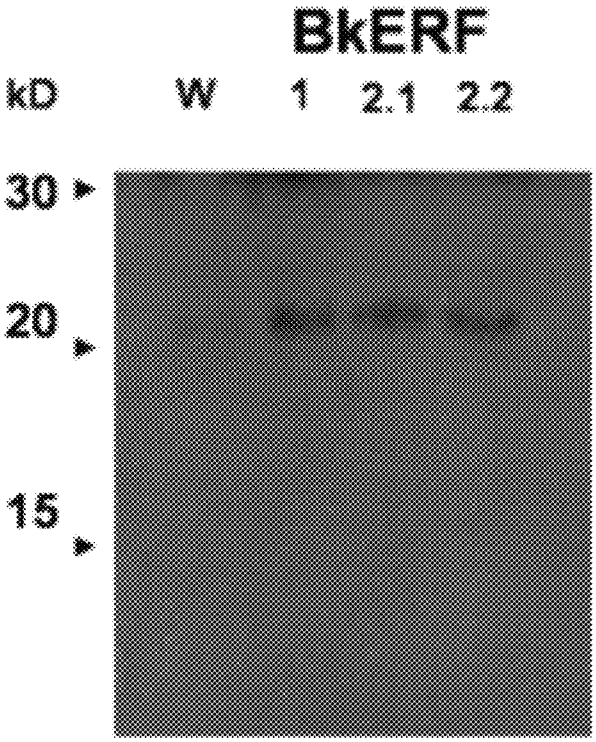
FIG. 6 Western analysis of the transgenic *B. kaoi* cells overexpressing the BkERFs using a BkERF2.2 antibody which recognizes all the known BkERFs.

The BkERF1, BkERF2.1, and BkERF2.2 genes are SEQ ID NO. 3, SEQ ID NO. 1 and SEQ ID NO. 2 respectively. The coding region of BkERFs was cloned into the multiple cloning site of the binary vector under the CaMV 35S promoter and the nopaline synthase termination sequence. The resulting vector was introduced into the *Agrobacterium tumefaciens* which was introduced into the cells of *B. kaoi*. The *B. kaoi* cells overexpressed BkERFs genes were observed using Western blot. FIG. 6 shows the application of BkERF2.2 antibody which was used to identify the known fragment of BkERFs protein.

Experiments of Inhibition to Bacteria and Enhancement of Resistance

Bacteria suspension of a concentration about $10^8$ cfu/ml was made from bacteria cultured 1-2 days with culture medium, and inoculated to 0.2 g BkERF transformed calli then grown in a 25° C. incubator. After six days, the calli was homogenized in 10 mM magnesium sulfate. Serial dilution of the bacteria was prepared and spread on nutrient agar plate containing 50 mg/L rifampicin. The plates were put in a 28° C. incubator for two days and then the numbers of bacteria were calculated.

Results

BkERFs Increase the Transcripts of Pathogen-Related Genes

Figure 7:
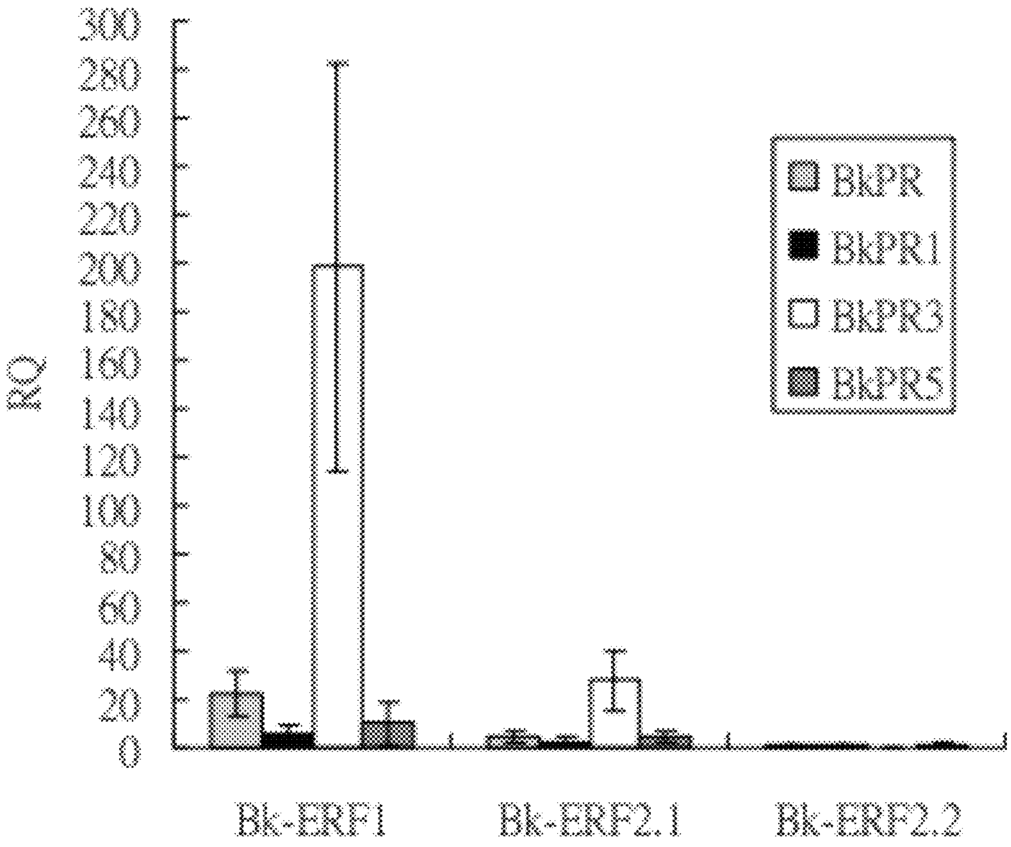
FIG. 7 Analysis of the mRNA levels of pathogen-related genes in the *B. kaoi* cells overexpressing the BkERFs using the real-time quantitative RT-PCR.

FIG. 7 showed the expression pathogen-related genes in *B. kaoi* cells overexpressing the BkERFs, which was performed with the real-time quantitative RT-PCR analysis.

BkERFs Help Cells Inhibit Bacteria

Figure 8A:
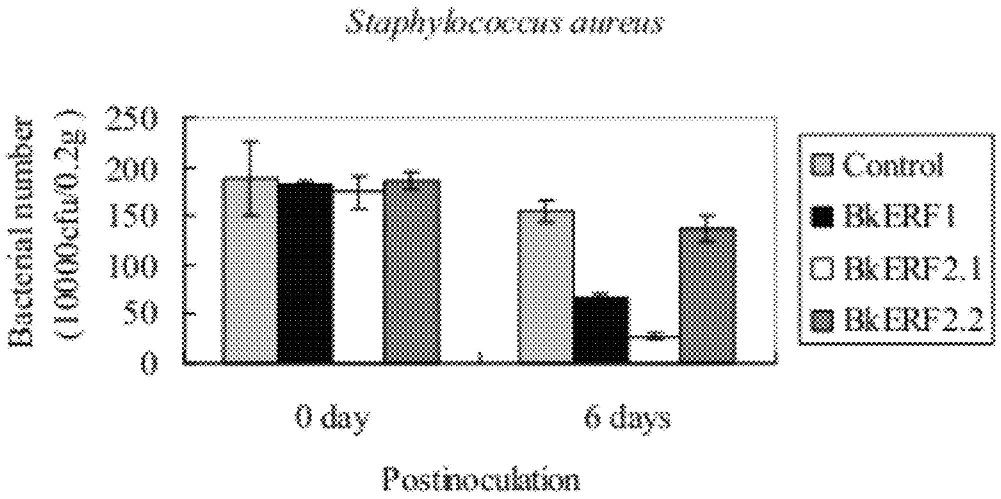
FIG. 8 The transformed *B. kaoi* cells overexpressing the ERF1 (black column), ERF2.1 (white column) and ERF 2.2 (dark gray column) were infected with *Staphylococcus aureus* (A) and *Psudomonas syringe* (B), respectively. The growth of bacteria in the transformed cells was inhibited as shown by bacterial numbers at 6 days after infection, which can further explain that the BkERFs transformed cells have the ability to resist bacteria.
Figure 8B:
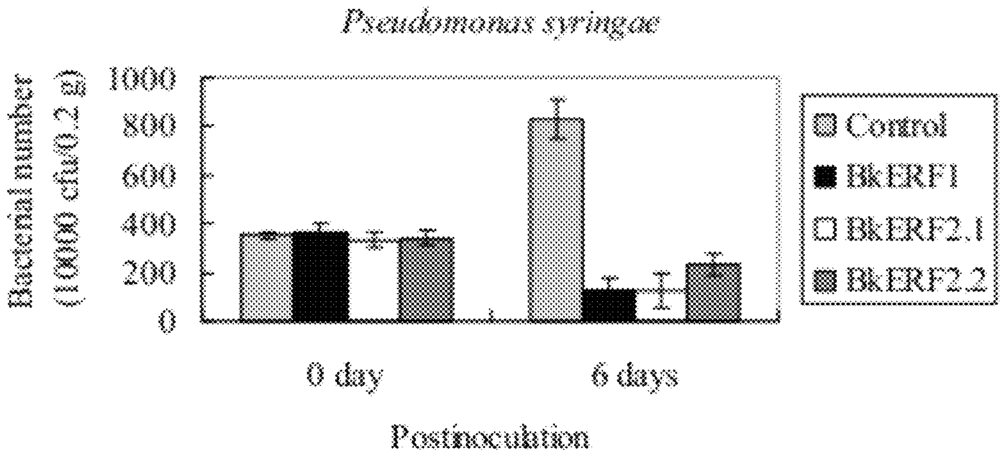
Figure 9:
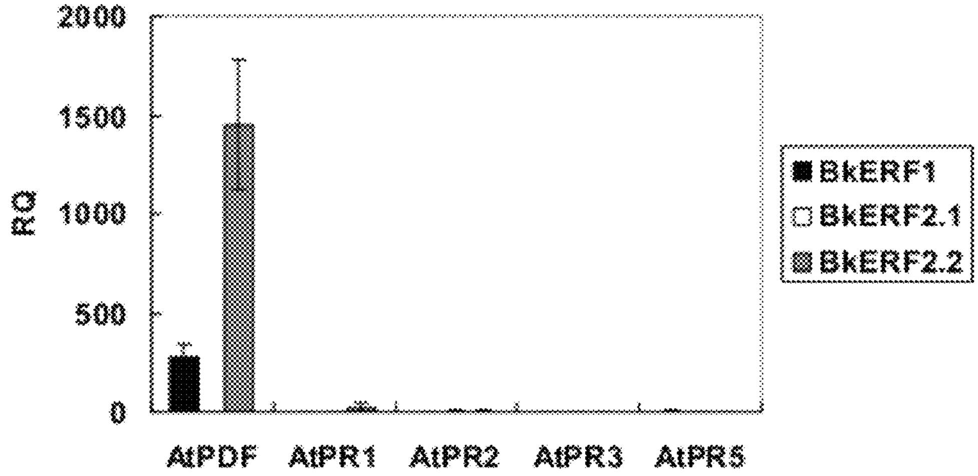
FIG. 9 Analysis of the mRNA levels of a defensin and 4 pathogen-related genes in the transgenic *Arabidopsis* overexpressing the BkERFs using the real-time RT-PCR.

FIG. 8 showed that the transformed *B. kaoi* cells overexpressing ERF1, ERF2.1 and ERF2.2 were infected with *Staphylococcus aureus* and *Psudomonas syringe*, respectively. The growth of bacteria in the transformed cells was inhibited as shown by bacterial numbers at 6 days after infection. This result can further explain that the BkERFs transformed cells have the ability to resist bacteria.

BkERFs Help Plants to Resist Pathogens

BkERFs genes were stably transformed into *Arabidopsis*. The transformed plant showed an increase in the transcripts of defensin and 4 pathogen-related genes.

What is claimed is:

1. An isolated polynucleotide having SEQ ID NO: 1, SEQ ID NO: 2 or SEQ ID NO: 3.

2. A method of generating a transgenic plant having enhanced pathogen resistance and inhibition, comprising inserting the polynucleotide of claim 1 into a vector, transforming the vector into a microorganism, which is introduced into the plant using microorganism-mediated transformation.

3. The method of claim 2, wherein the pathogen is bacteria.

4. The method of claim 3, wherein the bacteria is *Staphylococcus aureus*.

5. The method of claim 3, wherein the bacteria is *Pseudomonas syringae*.

6. The method of claim 2, wherein the microorganism is *Agrobacterium tumefaciens*.

7. The method of claim 2, wherein the plant is selected from *Bupleurum, Arabidopsis*, cotton, oat, pepper or sugarcane.

8. A transgenic plant, which is prepared by the method of claim 2.

9. The transgenic plant of claim 8, which is *Bupleurum, Arabidopsis*, cotton, oat, pepper or sugarcane.

* * * * *

SEQUENCE LISTING

<160> NUMBER OF SEQ ID NOS: 3

<210> SEQ ID NO 1
<211> LENGTH: 693
<212> TYPE: DNA
<213> ORGANISM: Bupleurum kaoi
<220> FEATURE:
<221> NAME/KEY: gene
<222> LOCATION: (1)..(693)

<400> SEQUENCE: 1

```
atgatgaact ttcaagaaaa ttctgggttt gattcagctg actttgatct tcttgaatcc     60

atcagacaac atcttctaag cgatgttgaa gaagcaaatt tcaacattcc ggctacgtac    120

tgcttgagtg atgaaaattc cggctatcga atgtttatat catcattttc cgacacagtt    180

gttgtgaagc cggagccgga gattgaggtg tctgaaatta aaagtgttga ggcgacggcg    240

gcgccggaaa aagggaagca ttacagagga gtaagacaac ggccgtgggg gaagttcgcg    300

gcggagatta gagatccggc aaaggatggg gcccgcgtgt ggctaggcac gtatgaaacg    360

gcagaggatg ctgcgttagc ttatgaccag gcagcgtacc gcatgcgcgg ctcacgtgcc    420

atgttgaact ttccactccg ggtgaattcc ggcgagccgg agccgaagcg tataatgtcg    480

aagagatcac tggtggcgct caattcggcg gcggtttctt cgtcgacgac aatgtcgtcg    540

tctacttgtt cggattcatc gtcgtcggtt tcaatgccga agaggcagaa gaagacggcg    600

gcgccggcga atgtgatggt gttggagaga acggagagtg tggaagttga ttcatttgaa    660

aaatggttga tggggaatga gtttgttttt taa                                 693
```

<210> SEQ ID NO 2
<211> LENGTH: 702
<212> TYPE: DNA
<213> ORGANISM: Bupleurum kaoi
<220> FEATURE:
<221> NAME/KEY: gene
<222> LOCATION: (1)..(702)

<400> SEQUENCE: 2

```
atgtcggaaa tatgtttgcc cgctttatat aatcgaagct caagttttag cagtttgatg     60

acatgtttat catcagagac atggggtgat ttgccgctta aagaagatga ttctgaagat    120

atggttatat acaactttct acgtgacgcc gttacggctg gttggacgcc gttcaatttc    180

acagctaccg acgttattaa gcccgagcca gccgatgaaa ttaagccgga aagtgttact    240

ccaactccga tctcgattcc gacaacatcg gcggcgtcgc cggcgaaggg aaggcactac    300

agaggtgtaa ggcaaaggcc gtggggaaag ttcgcggcgg agattagaga cccggctaag    360

aacggcgcca gagtttggct cggaacatac gaaacggcgg aggaagctgc gttagcctat    420

gacagagctg cttacaggat gcgcggttca aaggctttgt taaattttcc gcaccgagcc    480

ggttcgaatg aaccggaccc ggttcggatc actgctaaga gaaaatgttc acctgagccg    540

accggttcag gttcgggcag tgagtctcct aagcgaagaa agagaggagg agtatcggct    600

gatcagaaaa ccgaaccgga agtggagagc cggtccaatg cgtgtccaat taagtgcgag    660

ataagacaaa tgccagttgg agaacaatta ttggtcagct ag                       702
```

<210> SEQ ID NO 3
<211> LENGTH: 633
<212> TYPE: DNA
<213> ORGANISM: Bupleurum kaoi
<220> FEATURE:

-continued

```
<221> NAME/KEY: gene
<222> LOCATION: (1)..(633)

<400> SEQUENCE: 3

atggatacta atttctcacc ggaatattca tcgggttcga taccagattc tttcggatca     60

tatgatcttg atttcgatat tacttcactg ccatttgatt ttaatgattc cgaagaaatg    120

ttactctttg gcattttatc cgaaaatgca ccagaaccac attcttctag tgaaatcaaa    180

gaagaagata cgagtttaag tccaaaaaac gttgaaaaca agaaagaaaa ggcgtataga    240

ggtgtccgta gacgaccatg ggaaaatttt gctgcagaaa ttagagattc gacaagaaat    300

ggcattcggg tttggcttgg aacatttgat gatgctgaga ctgcggcgat ggcttatgat    360

caagctgcat tttcaatgaa agggccactg gctacactta attttccagt ggatagagtt    420

aaagagtcat ttgaagagat gaagtgtggg cttgaacaag ggtgttctcc ggtgatggca    480

ttgaagagaa aacattccct tagaaggaaa tctgtttgcc ggaaaaacaa gaaaaagaat    540

ggtcaatcag aaaatgttgt ggtttttgag gatttgggtg cagagtatct agaagaattg    600

ttgagttcat ctctaagttg tgcagtttgg taa                                 633
```